(12) United States Patent
Joseph

(10) Patent No.: US 12,277,814 B2
(45) Date of Patent: Apr. 15, 2025

(54) MEDICAL ANALYZER AND DIAGNOSTIC SAMPLE PROFILER

(71) Applicant: iFirst Medical Technologies, Inc., Honolulu, HI (US)

(72) Inventor: Luke B. Joseph, Honolulu, HI (US)

(73) Assignee: iFirst Medical Technologies, Inc., Honolulu, HI (US)

( * ) Notice: Subject to any disclaimer, the term of this patent is extended or adjusted under 35 U.S.C. 154(b) by 0 days.

(21) Appl. No.: 17/759,161

(22) PCT Filed: Jan. 28, 2021

(86) PCT No.: PCT/US2021/015491
§ 371 (c)(1),
(2) Date: Jul. 20, 2022

(87) PCT Pub. No.: WO2021/154995
PCT Pub. Date: Aug. 5, 2021

(65) Prior Publication Data
US 2023/0086165 A1    Mar. 23, 2023

Related U.S. Application Data

(60) Provisional application No. 62/967,551, filed on Jan. 29, 2020.

(51) Int. Cl.
*G07C 5/08*    (2006.01)
*G11B 31/00*    (2006.01)

(52) U.S. Cl.
CPC .......... *G07C 5/0891* (2013.01); *G11B 31/006* (2013.01)

(58) Field of Classification Search
None
See application file for complete search history.

(56) References Cited

U.S. PATENT DOCUMENTS

| | | |
|---|---|---|
| 3,053,078 A | 9/1962 | Jewett |
| 3,520,659 A | 7/1970 | Steinberg et al. |
| | (Continued) | |

FOREIGN PATENT DOCUMENTS

| | | |
|---|---|---|
| EP | 0525273 B1 | 10/1996 |
| JP | 2001/263533 | 9/2001 |
| | (Continued) | |

OTHER PUBLICATIONS

Invitation to Pay Additional Fees, PCT/US2021/015491; Apr. 9, 2021; 3 pages.

(Continued)

*Primary Examiner* — Hung Q Dang
(74) *Attorney, Agent, or Firm* — Knobbe, Martens, Olson & Bear, LLP

(57) ABSTRACT

A medical analyzer and coagulation profiler performs various interrogations on specimens. A motor with reduction gearing moves and a video camera observes the samples, the cartridges or parts thereof. Changes in images are compared and recorded with a central processor that controls a display. Power supply, temperature controller, motor and gearing are mounted in a box which attaches to a smartphone. The smartphone provides the video camera, illumination and central processor that control the movement, temperature and display. The device makes testing simpler for small hospitals, clinics, ambulances, remote locations and individuals and controls a number of parallel or serial devices operating simultaneously or sequentially. A cartridge insertion actuates a circular motion to generate a blood profile based on changes. Change is analyzed with a video camera and processor such as in a smartphone and is plotted to show an amplitude and time. A smartphone provides a specific movement pattern.

19 Claims, 40 Drawing Sheets

(56) References Cited

U.S. PATENT DOCUMENTS

| | | |
|---|---|---|
| 3,650,698 A | 3/1972 | Adler |
| 3,695,842 A | 10/1972 | Mintz |
| 3,704,099 A | 11/1972 | Sanz |
| 3,836,333 A | 9/1974 | Mintz |
| 3,861,197 A | 1/1975 | Adler |
| 3,875,791 A | 4/1975 | Fitzgerald et al. |
| 4,045,999 A | 9/1977 | Palmer |
| 4,081,242 A | 3/1978 | Girolami |
| 4,148,216 A | 4/1979 | Do et al. |
| 4,193,293 A | 3/1980 | Cavallari |
| 4,317,363 A | 3/1982 | Shen |
| 4,328,701 A | 5/1982 | Mau-Tang et al. |
| 4,334,424 A | 6/1982 | Kepes |
| 4,341,111 A | 7/1982 | Husar |
| 4,498,782 A | 2/1985 | Proctor et al. |
| 4,706,207 A | 11/1987 | Hennessy et al. |
| 4,918,984 A | 4/1990 | Martinoli et al. |
| 4,964,728 A | 10/1990 | Kloth et al. |
| 5,016,469 A | 5/1991 | Henderson |
| 5,071,247 A | 12/1991 | Markosian et al. |
| 5,110,727 A | 5/1992 | Oberhardt |
| 5,138,872 A | 8/1992 | Henderson |
| 5,154,082 A | 10/1992 | Mintz |
| 5,163,317 A | 11/1992 | Ono et al. |
| 5,181,415 A | 1/1993 | Esvan et al. |
| 5,217,860 A | 6/1993 | Fahy et al. |
| 5,223,227 A | 6/1993 | Zuckerman |
| 5,350,676 A | 9/1994 | Oberhardt et al. |
| 5,523,238 A | 6/1996 | Varon et al. |
| 5,629,209 A | 5/1997 | Braun et al. |
| 5,777,215 A | 7/1998 | Calatzis et al. |
| 5,789,664 A | 8/1998 | Neel et al. |
| 6,016,712 A | 1/2000 | Warden et al. |
| 6,103,196 A | 8/2000 | Yassinzadeh et al. |
| 6,136,271 A | 10/2000 | Lorincz et al. |
| 6,165,795 A | 12/2000 | Mize et al. |
| 6,225,126 B1 | 5/2001 | Cohen et al. |
| 6,573,104 B2 | 6/2003 | Carr et al. |
| 6,586,259 B1 | 7/2003 | Mahan et al. |
| 6,591,663 B1 | 7/2003 | Murray et al. |
| 6,591,664 B2 | 7/2003 | Litton |
| 6,613,573 B1 | 9/2003 | Cohen |
| 6,767,511 B1 | 7/2004 | Rousseau |
| 6,898,532 B1 | 5/2005 | Toh et al. |
| 6,989,272 B1 | 1/2006 | Savion et al. |
| 7,179,652 B2 | 2/2007 | Cohen et al. |
| 7,182,913 B2 | 2/2007 | Cohen et al. |
| 7,211,438 B2 | 5/2007 | Toh et al. |
| 7,235,213 B2 | 6/2007 | Mpock et al. |
| 7,262,059 B2 | 8/2007 | Zheng et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,524,670 B2 | 4/2009 | Cohen et al. |
| 7,732,213 B2 | 6/2010 | Cohen et al. |
| 7,754,489 B2 | 7/2010 | Cohen |
| 8,076,144 B2 | 12/2011 | Cohen |
| 8,211,381 B2 | 7/2012 | Ricci |
| 8,322,195 B2 | 12/2012 | Glauner et al. |
| 8,365,582 B2 | 2/2013 | Sakai |
| 8,383,045 B2 | 2/2013 | Schubert et al. |
| 8,425,840 B2 | 4/2013 | Hosokawa |
| 8,448,499 B2 | 5/2013 | Schubert et al. |
| 8,450,078 B2 | 5/2013 | Dennis et al. |
| 8,795,210 B2 | 8/2014 | Talish et al. |
| 8,877,710 B2 | 11/2014 | Johansson et al. |
| 9,046,512 B2 | 6/2015 | Djennati et al. |
| 9,063,161 B2 | 6/2015 | Dennis et al. |
| 10,184,872 B2 | 1/2019 | Sakai |
| 10,739,239 B1 | 8/2020 | Joseph et al. |
| 10,823,743 B1 | 11/2020 | Joseph et al. |
| 11,598,707 B1 | 3/2023 | Joseph et al. |
| 2001/0022948 A1 | 9/2001 | Tuunanen |
| 2002/0124634 A1 | 9/2002 | Litton |
| 2002/0168294 A1 | 11/2002 | Carr et al. |
| 2003/0064505 A1 | 4/2003 | Harttig |
| 2003/0064507 A1 | 4/2003 | Gallagher et al. |
| 2003/0069702 A1 | 4/2003 | Cohen et al. |
| 2003/0073244 A1 | 4/2003 | Cohen et al. |
| 2003/0131500 A1 | 7/2003 | Kline et al. |
| 2003/0180824 A1 | 9/2003 | Mpock et al. |
| 2003/0199428 A1 | 10/2003 | Carr |
| 2004/0131500 A1 | 7/2004 | Chow |
| 2004/0161855 A1 | 8/2004 | Kvasnik et al. |
| 2004/0203163 A1 | 10/2004 | Cohen et al. |
| 2004/0224419 A1 | 11/2004 | Zheng et al. |
| 2005/0180886 A1 | 8/2005 | Bote Bote |
| 2005/0233460 A1 | 10/2005 | Clague et al. |
| 2005/0233466 A1 | 10/2005 | Wright et al. |
| 2005/0255601 A1 | 11/2005 | Nippoldt et al. |
| 2006/0034734 A1 | 2/2006 | Schubert et al. |
| 2007/0059840 A1 | 3/2007 | Cohen et al. |
| 2007/0158246 A1 | 7/2007 | Davies et al. |
| 2007/0184508 A1 | 8/2007 | Cohen et al. |
| 2007/0291345 A1 | 12/2007 | Kumar et al. |
| 2008/0011107 A1 | 1/2008 | Leventhal et al. |
| 2008/0015477 A1 | 1/2008 | Talish et al. |
| 2008/0038828 A1 | 2/2008 | Cohen et al. |
| 2008/0206880 A9 | 8/2008 | Clague et al. |
| 2008/0233554 A1 | 9/2008 | Sehgal et al. |
| 2008/0261261 A1 | 10/2008 | Grimes et al. |
| 2008/0294068 A1 | 11/2008 | Briggs et al. |
| 2009/0198120 A1 | 8/2009 | Gurbel |
| 2009/0304547 A1 | 12/2009 | Werner et al. |
| 2010/0139375 A1 | 6/2010 | Johns et al. |
| 2010/0154520 A1 | 6/2010 | Schubert et al. |
| 2010/0170327 A1 | 7/2010 | Glauner et al. |
| 2010/0184201 A1 | 7/2010 | Schubert et al. |
| 2010/0267066 A1 | 10/2010 | Hosokawa et al. |
| 2010/0268094 A1 | 10/2010 | Hasling et al. |
| 2011/0036150 A1 | 2/2011 | Sakai |
| 2011/0151491 A1 | 6/2011 | Dennis et al. |
| 2011/0223663 A1 | 9/2011 | Sehgal et al. |
| 2011/0268732 A1 | 11/2011 | Johansson |
| 2012/0028342 A1 | 2/2012 | Ismagilov et al. |
| 2012/0111097 A1 | 5/2012 | Sierro |
| 2012/0294767 A1 | 11/2012 | Viola et al. |
| 2013/0195722 A1 | 8/2013 | Mitchell et al. |
| 2013/0267017 A1 | 10/2013 | Dennis et al. |
| 2014/0020475 A1 | 1/2014 | Inoue et al. |
| 2014/0047903 A1 | 2/2014 | Sakai |
| 2014/0273249 A1 | 9/2014 | Yuan et al. |
| 2015/0024473 A1* | 1/2015 | Wu .......... G01N 11/14 435/287.1 |
| 2015/0118691 A1 | 4/2015 | De Laat et al. |
| 2015/0226725 A1 | 8/2015 | Gill et al. |
| 2015/0253343 A1 | 9/2015 | Pearce et al. |
| 2015/0301018 A1 | 10/2015 | Dayel et al. |
| 2015/0304555 A1* | 10/2015 | Ehrenkranz .......... H04N 23/56 348/370 |
| 2015/0305681 A1 | 10/2015 | Nadkarni |
| 2017/0010205 A1 | 1/2017 | Hayashi et al. |
| 2017/0283845 A1 | 10/2017 | Holmes et al. |
| 2019/0219490 A1* | 7/2019 | Hosokawa .......... G01N 33/86 |
| 2021/0302412 A1 | 9/2021 | Joseph |
| 2023/0086165 A1 | 3/2023 | Joseph |

FOREIGN PATENT DOCUMENTS

| | | |
|---|---|---|
| KR | 101460673 | 11/2014 |
| WO | WO 2013/067536 | 5/2013 |
| WO | WO 2015/073941 | 5/2015 |
| WO | WO 2020/023726 | 1/2020 |
| WO | WO 2021/154995 | 8/2021 |

OTHER PUBLICATIONS

International Search Report; PCT/US2021/015491; Jun. 28, 2021; 16 Pages.
Castro-Paacio, J.C. et al, American Journal of Physics 2013, 81, 472-475.
Crocker, J. C. et al, Journal of Colloid and Interface Science 1996, 179, 298-310.

(56) References Cited

OTHER PUBLICATIONS

Gasull, A. et al, IEEE 1992, 1948-1949.
"GPU-accelerated video proccessing on Mac and iOS", Sunset Lake Software, www.sunsetlakesoftware.com/2010/10/22/gpu-accelerated-video-processing-mak-and-ios; Oct. 22, 2010.
Hortschitz, W. et al, IEEE Sensors Journal 2011, 11, 2805-28-12.
International Search Report; PCT/US2019/043400; Oct. 2, 2019; 13 Pages.
Muller, O. et al., Macromolecues 1991, 24, 3111-3120.
Shore-Lesserson, L. et al, Anesthesia & Analgesia 1999, 88, 312-319.
Smith, Z. J. et al, PLOS One 2011, 11, paper e17150, 11 pages.
StirBars.com, "Stir Bar Price List" accessed Apr. 14, 2015 in 13 pages (http://www.stirbars.com/magnetic-stirbar-prices.htm).
Ziemann, F. et al, Biophysical Journal 1994, 66, 2210-2216.
Extended European Search Report for 21747890.8 mailed May 31, 2024 in 8 pages.
Anonymous: "Rhea-Line Oscillating Disc Rheometer", 2013, XP093158464, Retrieved from the Internet: URL:https://www.prescott-instruments.com/wp-contenVu ploads/201 5/09/Rheoline-ODR.pdf [retrieved on May 2, 2024].

\* cited by examiner

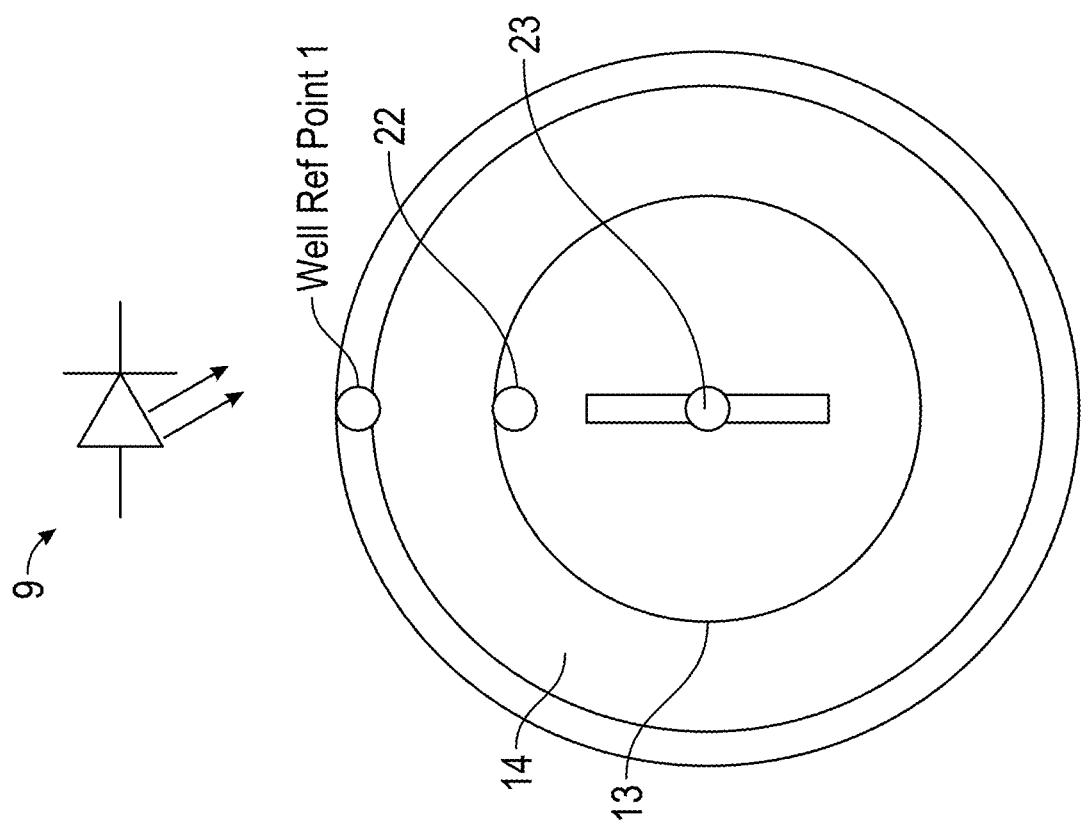

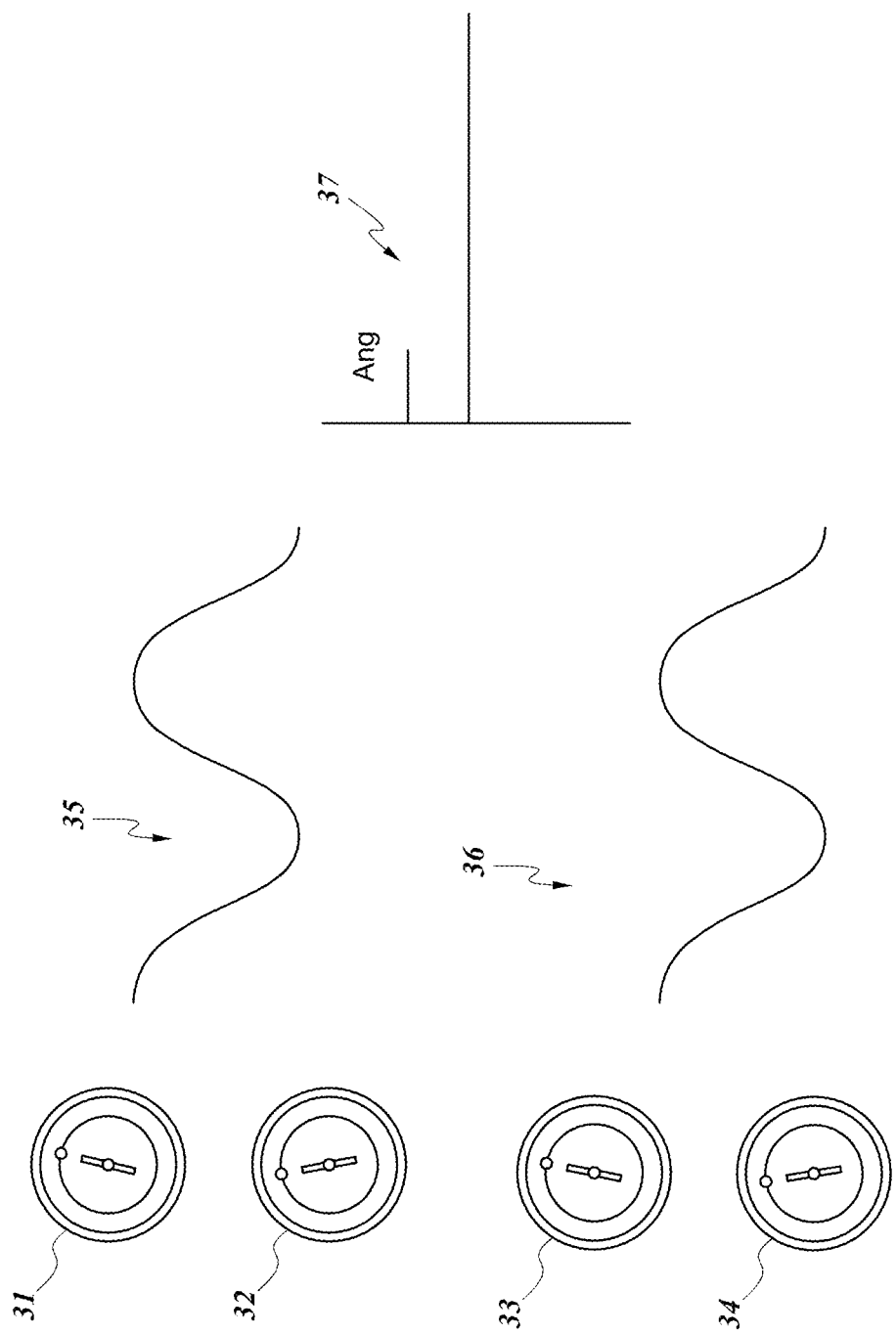

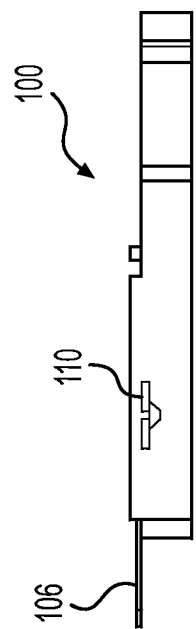
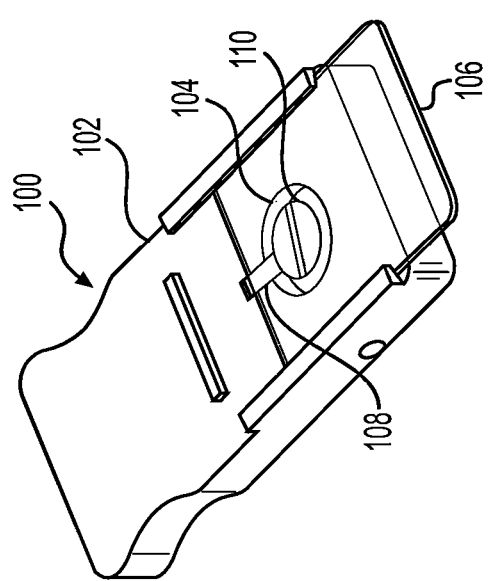
FIG. 11B
FIG. 11A

A liquid in a capillary tube forms a meniscus that can be described by the function $$y = ax^2 + bx + c,$$

where the $x$ and $y$ axes are oriented as shown in the figure below.

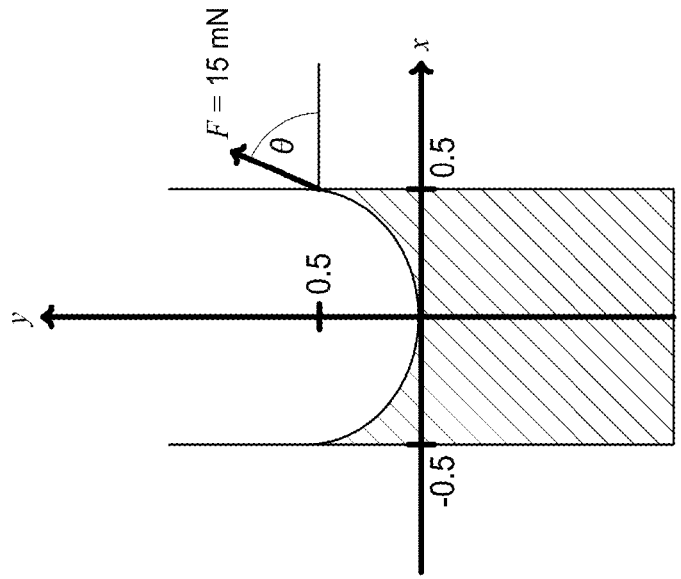

(a) Use the information given, and the diagram to determine $a$, $b$ and $c$ and hence write the function describing the meniscus.

(b) Find the derivative of the function, and hence determine the angle $\theta$ in degrees.

(c) The force F with magnitude $F$ and direction $\theta$, represents the total surface tension force around the circumference on the liquid in the tube. The vertical component of F holds up the liquid in the tube above the liquid outside the tube.

FIG. 21

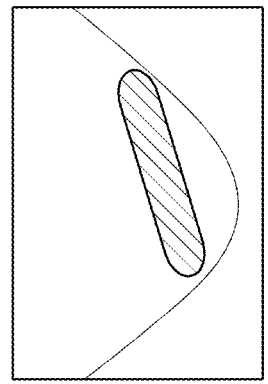
Too hydrophilic
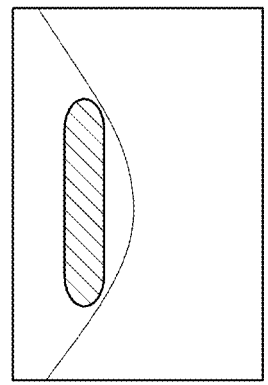
Just right
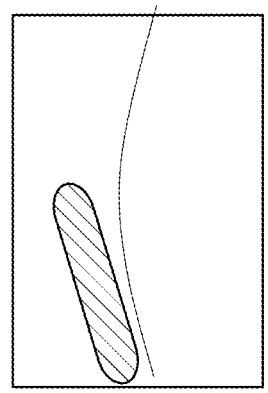
Too hydrophobic
FIG. 22

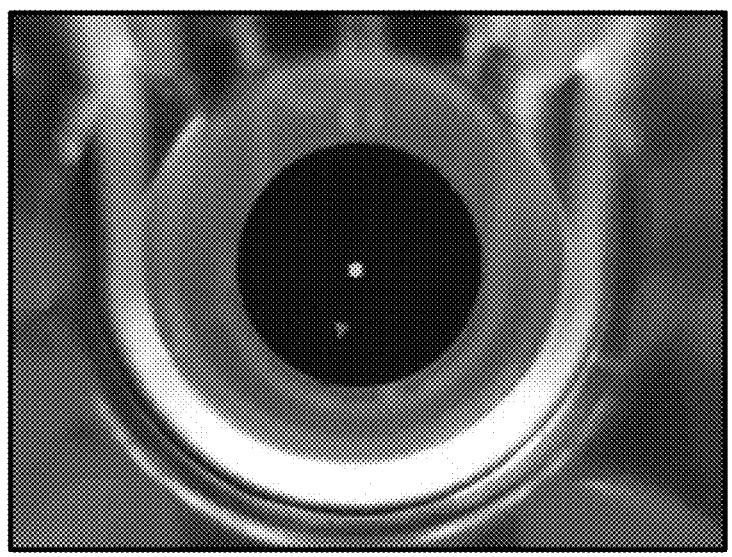
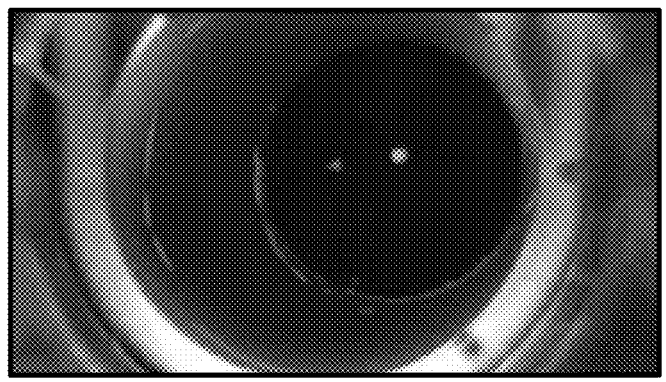
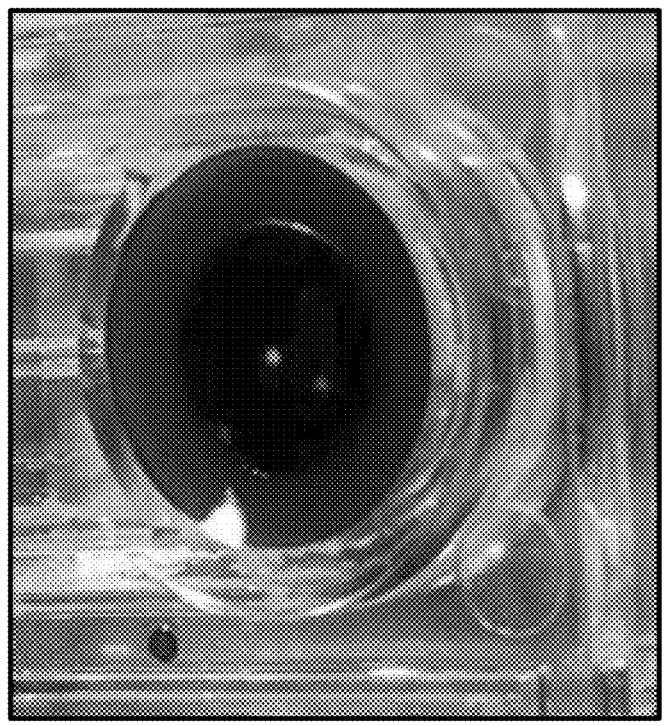
FIG. 23

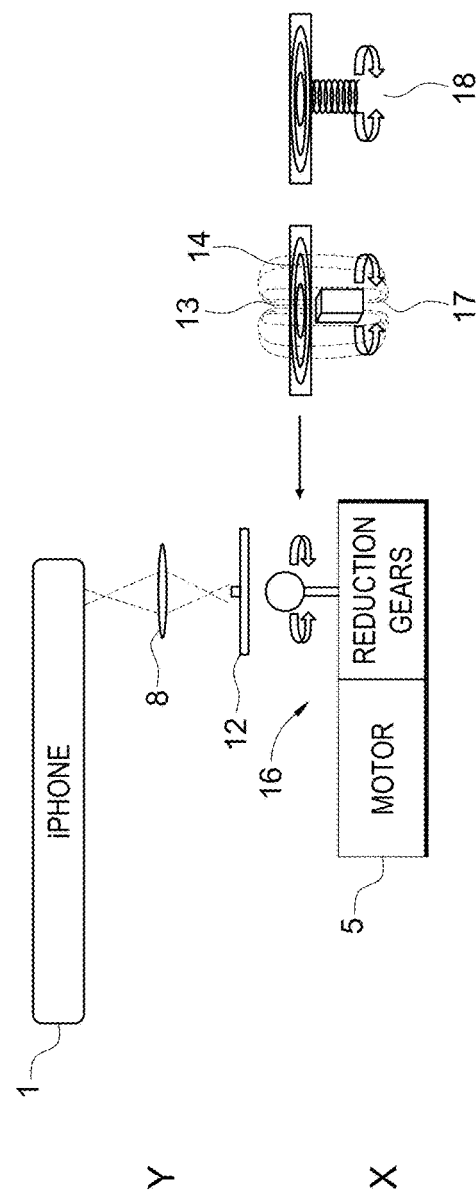
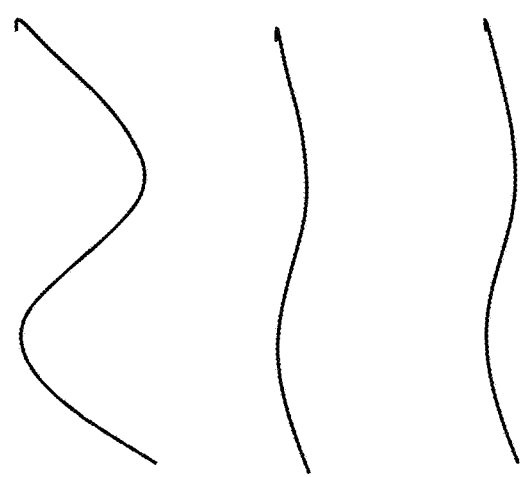
FIG. 25

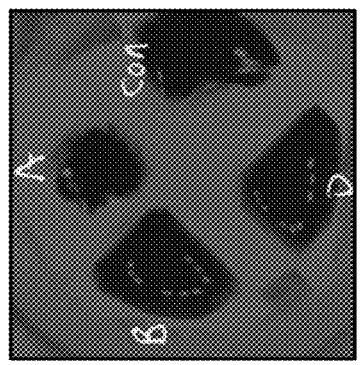
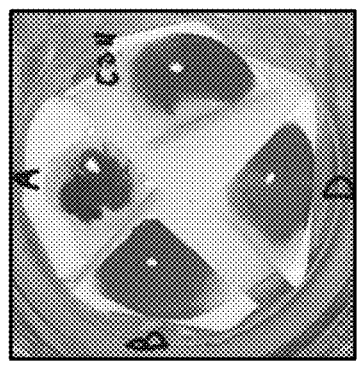
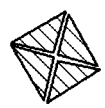
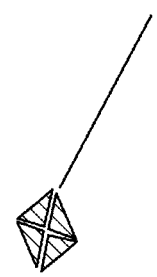
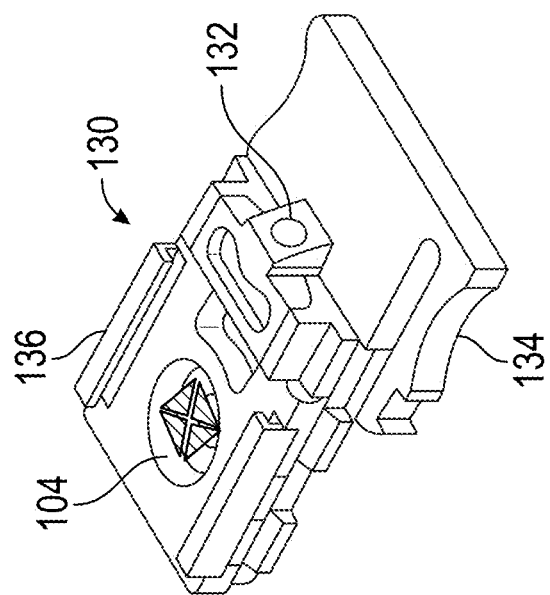
FIG. 26

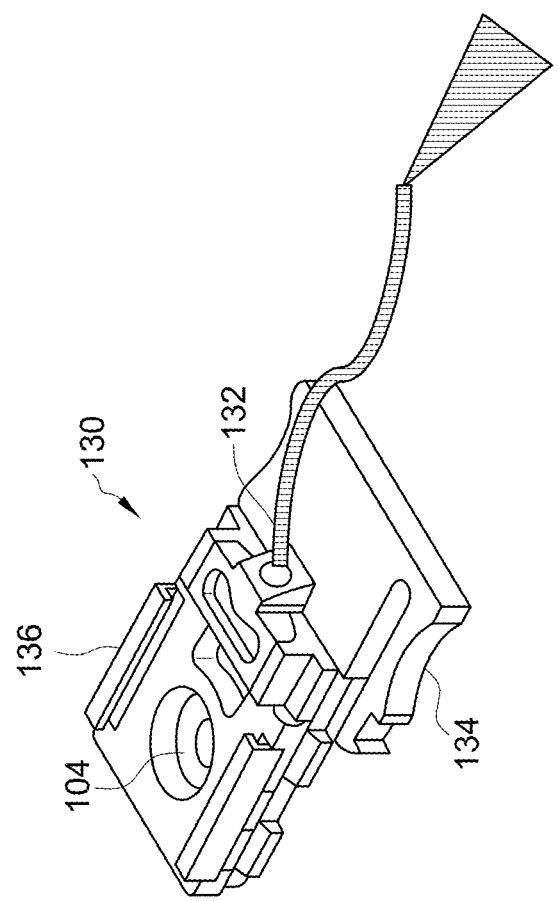
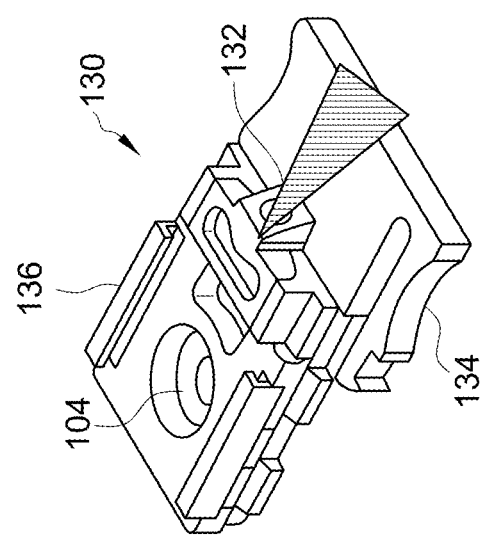
FIG. 27

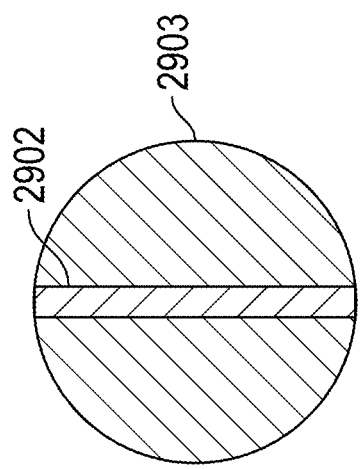
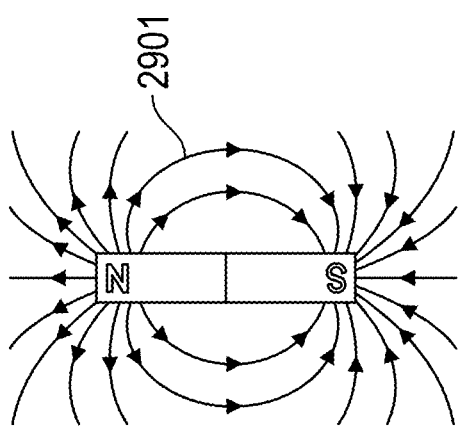
FIG. 29A
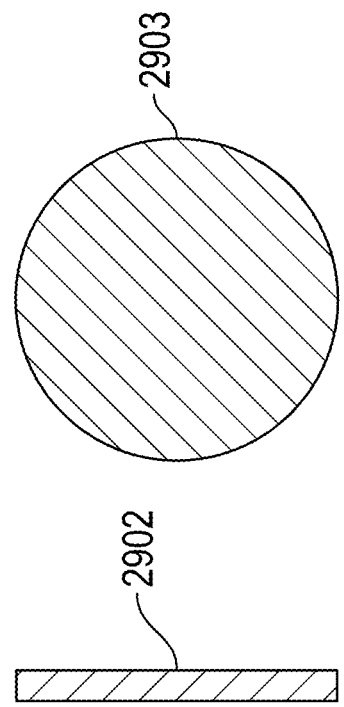
FIG. 29B

MEDICAL ANALYZER AND DIAGNOSTIC SAMPLE PROFILER

This application is the U.S. National Phase under 35 U.S.C. § 371 of International Application No. PCT/US2021/015491, filed Jan. 28, 2021, titled MEDICAL ANALYZER AND DIAGNOSTIC SAMPLE PROFILER, which claims the benefit under 35 U.S.C. § 119 as a nonprovisional of U.S. Prov. App. No. 62/967,551 filed on Jan. 29, 2020, which is hereby incorporated by reference in its entirety. This application relates to U.S. patent application Ser. No. 14/526,034 filed on Oct. 28, 2014; U.S. Ser. No. 14/526,057 filed on Oct. 28, 2014; and PCT App. No. PCT/US2019/043400 filed on Jul. 25, 2019, each of, which is hereby incorporated by reference in its entirety.

BACKGROUND

Five million people around the world die of trauma on an annual basis. Up to 20% of these deaths are preventable with better control of bleeding. In these types of traumatic injury, the incidences of coagulation abnormalities are high. For example, natural supplies of proteins such as Factor VII are quickly depleted after trauma, which can quickly lead to hemorrhage-related death. Detecting these abnormalities quickly after the trauma often can be a predictor of the patient's mortality. These diagnostics can be a decision aid for providers and provide feedback for lifesaving actions, such as transfusions.

Although techniques such as prothrombin time (PT) and partial thromboplastin time (PTT) can test coagulation, only the first state of coagulation and plasma hemostasis are tested rather than coagulocompetence. In addition it has been shown that PT and PTT tests do not predict coagulation abnormalities as effectively as coagulation profiles, such as thrombelastography (TEG) shown in FIG. 10A. In addition separating the plasma complicates the blood processing and adds steps to the coagulation initiation.

Other coagulation profiling techniques such as thrombelastography and rotational thromboelastometry (ROTEM) shown in FIG. 10B provide a more complete coagulation profile by using whole blood. The use of whole blood includes the role of platelets, blood factors and phospholipids in the coagulation cascade. Unfortunately both standard coagulation tests (PT, PTT, etc.), and newer systems such as TEG and ROTEM, require relatively large equipment, controlled conditions and trained technicians to perform tests. These limitations prevent these diagnostic tools from being at the point of injury (POI).

In order to most effectively treat traumatic injuries, it can be important to diagnose coagulation abnormalities at the POI, ideally by first responders such as paramedic and emergency medical technicians (EMT) (FIG. 9) Paramedics and EMTs could rapidly evaluate the coagulopathy and obtain guidance in using blood products or administration of coagulation related drugs. In addition, further integration of other coagulation relevant assays, such as complete blood count (CBC) or hematocrit (HCT), base deficit, platelet count, and $PaO_2$ with a TEG-like profile could be an invaluable addition to point-of-care diagnostics.

Needs exist for improved base medical analyzers and coagulation profilers.

SUMMARY

Some embodiments of the invention can solve the existing problems by providing new base medical analyzers and coagulation profilers that can be available to be quickly used.

An example of embodiments of the invention can include a new cartridge based biological microelectromechanical system (BioMEMS) that rotates back and forth in a circular motion in direct contact to a blood sample, while the blood coagulates. This rotation changes over time as the blood coagulates in the sample. The change in motion is analyzed through a video camera (such as a smartphone, e.g., IPHONE camera (Apple, Inc., Cupertino, CA) and then is plotted to show an amplitude over time. The plot of motion over time is indicative of particular forms of coagulation disorders. The rotating motion of the BioMEMS device is induced externally using a magnetic field. The rotation induced is not limited to a magnetic field but could be direct mechanical or electrostatic inducer of the rotation. The magnetic actuation is provided by a motor, servo or similar device that turns a magnet. The motor can be controlled mechanically or electronically, by the iPhone for example, to provide a specific pattern. In one case the pattern is about 4° 45' in 5 seconds. There can be a large range of patterns, dependent on application. In one case the profile is measured for about 30 to 60 minutes or more or less, however, time may vary depending on application. The motor can be controlled mechanically or electronically, by a portable computing device such as a smartphone, e.g., an iPhone for example, to provide a specific pattern. In one case the pattern is about 4° 45' in 5 seconds. Range of patterns include variations over a larger angular sweep and variations in time. In some embodiments the effective angular motion can be tracked in real time (e.g., within about 60 seconds, 30 seconds, 10 seconds, or less) and the angular sweep can be adjusted to maximize the desired motion induced and torque profile induced to the disk. An example of this would be to reduce the angular sweep of the magnet to follow the reduction in motion caused by coagulation. If a disk rotation reduction of 10 degrees is detected by the tracking algorithm the servo/motor could be adjusted to reduce the magnetic rotation by the same angle, e.g., 10 degrees. This angular reduction could also be captured in the algorithm plotting profile. This feedback technique would continue as the angular sweep continues to decrease. In this way, the sensitivity to the beginning of the clot is increased and this sensitivity is maintained since there is no excessive motion and the plotting algorithm scales to the reduction in motion. This scaling increases weight in amplitude represented by an angular change.

Use of a mobile device, such as an iPhone, has been demonstrated to show coagulation over time in the form of a coagulation profile. Some embodiments of the invention make the testing simpler by use of a cartridge and provides a method of having a large number of sequential tests to monitor a patient from POI to the emergency room (ER), operating room and recovery. The overall system and the cartridge can be very small. The use of cartridges in some embodiments of the invention simplifies the process as compared to conventional techniques. Being small and portable there is potential provided by some embodiments of the invention for a large number of parallel or serial devices operating simultaneously.

The system can comprise in some embodiments a handheld medical analyzer platform, which works with different disposable application cartridges to perform a variety of interrogations on specimen samples. One application includes attaching a biological microelectromechanicalsystem (BioMEMS) cartridge that generates blood coagulation profiles indicative of particular forms of coagulation disorders. The device makes coagulopathy testing simpler for small hospitals, clinics, ambulances, remote locations and individuals by use of a cartridge and permits for a larger number of parallel or serial devices operating simultaneously. One insertion of a cartridge actuates an oscillating circular motion to generate a blood coagulation profile based on a change in rotational motion as blood coagulates in a sample. Change in rotational motion is analyzed through a video camera such as in a smartphone and is plotted to show an amplitude over time. Actuation of the BioMEMS can be achieved by magnetic actuation of a motor controlled by an iPhone or a smart phone to provide a specific rotational pattern.

A liquid coagulation measuring device can include a case and a motor within the case. Gearing can be connected to the motor, or in some embodiments a servo, stepper motor, or other electromagnetic devices to induce the desired rotational profile. A magnet can be connected to the gearing and is configured for magnetic coupling to a movable element within a liquid well. A temperature controller can be used to control the temperature of the system, such as, for example, to be connected to the case and can be configured for controlling temperature of liquid in the liquid well. In some embodiments this temperature can be changed from a standard temperature, such as body temperature, e.g., around 37° C., to represent the patient's blood under test. For instance, if a patient is hypothermic or hyperthermic, the temperature of the control chamber can be controlled to match or substantially match the patient's actual temperature above or below normal body temperature, such as, for example, about 30° C., 31° C., 32° C., 33° C., 34° C., 35° C., 36° C., 37° C., 38° C., 39° C., 40° C., 41° C., 42° C., or ranges between any of the foregoing values.

A light source illuminates the movable element. In some embodiments, a UV light source can be used in conjunction with fluorescent tracking points to reduce background reflections and increase the contrast between the tracking points and the surroundings. This can advantageously help the tracking algorithm. In addition, LEDs that emit visible light can be used and turned on to help in the loading of the cartridge and injection of blood sample. In some embodiments, a recorder records movement of the movable element. A compact microscope can be configured for alignment with the liquid well and a video camera can be aligned with the compact microscope.

An attachment on the case can be configured for attaching to a smartphone having a video camera, a central processor and display. The attachment can be configured for aligning the video camera with the liquid well and the movable object.

The case can have a base and a cover. The base can have a bottom, sides and a top and a space in the top for positioning and holding a smartphone. The cover can be configured for covering border areas around a display face of the smartphone. The cover and the sides have complementary connections configured for holding the cover on the base and holding the smartphone within the case. One of the sides has an opening for receiving a cartridge with the well.

An elastomeric boot can surround the case and can be adapted for protecting the measuring device and the smartphone. The opening in the case can be configured for receiving the cartridge. A passage flows the liquid into the well through a cartridge port outside of the opening into one of the sides of the case. Reduction gearing is connected to the motor. The reduction gearing can be configured for reciprocating the magnet and thereby reciprocating the movable element. The reduction gearing can be configured for rotatably reciprocating the magnet and thereby rotatably reciprocating the movable element.

A liquid coagulation measuring device has a case and a reciprocating motor within the case. Reduction gearing can be connected to the motor. A contactless coupling can be connected to the reduction gearing and be configured for reciprocating a movable object in a well within the case. A temperature controller controls temperature within the case. A compact microscope in the case can be configured for magnifying an image of a movable object placed within the case.

A light source can illuminate the liquid or the movable object placed within the case. A video camera records movement of the movable object placed within the case. A power source can be connected to the motor, the light source and the video camera. A central processor (CPU) and graphics processing unit (GPU) can be connected to the power source and to the video camera and record a time from start of movement of the movable object until a change of the movement.

A display can be operably connected to the central processor. A smartphone connected to the case provides control of the light source, the video camera, the central processor and the display.

A housing, such as, for example, a rectangular box can include a bottom, a top and sides connecting the bottom and the top, supporting the smartphone on the top. A cover has a large opening with a frame for exposing the display and a start button of the smartphone while holding the smartphone on the box. An opening in at least one of the sides receives a cartridge having the liquid well. A pusher can be connected to the reduction gearing for pushing a lid on the cartridge and dropping the movable object into the well. To facilitate use by those preferring the right hand or left hand an embedded gyroscope can be used to auto rotate the screen to the user's preferred orientation. In this manner, in some cases the receiving side of the cartridge could be oriented in 4 variations changing by 90 degrees, including but not limited to two vertical positions and two horizontal positions.

A measuring device can be turned on. Internal temperature can be controlled in the device. A cartridge can be inserted into the device beneath a small microscope or a magnifier. A liquid sample can be injected into a well within the cartridge. The well or a movable device therein is reciprocated. The movable device is illuminated and is observed through the microscope with a video camera. Times of changes in movement of the movable device can be recorded. The movable device can be reciprocated with a contactless magnetic coupling. Time differentiation is recorded between a start of movement of the movable device and slowing and stopping of movement of the movable device. The movable device can be placed in the well after the injecting of the liquid sample. A power source can be connected to the heat controller and the motor. The smartphone provides the illuminating and a video camera and a central processor for recording times of changes in movement of the movable device and creating displays according to the changes in movement of the movable device.

A smartphone connected to the measuring device can be turned on to start the illuminating, the video camera and the central processor.

Disclosed herein are a method for measuring coagulation of a liquid, comprising: turning on a measuring device, controlling internal temperature in the device, inserting a cartridge into the device, injecting a liquid sample into a well within the cartridge, the well comprising a sidewall and a floor, wherein the well floor is relatively hydrophilic, and the well wall is relatively hydrophobic with respect to the well floor; providing a contactless magnetic coupling, reciprocating the well or a movable device within the well with the magnetic coupling, illuminating the movable device, observing the movable device with a video camera, and recording times of changes in movement of the movable device.

In some configurations, the reciprocating comprises reciprocating the movable device with a contactless magnetic coupling, and the recording comprises recording time differentiation between a start of movement of the movable device and slowing and stopping of movement of the movable device.

In some configurations, the method further comprises placing the movable device in the well after the injecting of the liquid sample.

In some configurations, the turning on comprises connecting a power source to the heat controller and to a motor for the reciprocating, and starting the illuminating and a video camera and a central processor for recording times of changes in movement of the movable device and creating displays according to the changes in movement of the movable device.

In some configurations, starting the illuminating, the video camera and the central processor comprises turning on a smartphone connected to the measuring device. In some embodiments, the smartphone can be configured to turn on the illumination, video camera, central processor, and graphics processor.

Also disclosed herein is a method for measuring coagulation of a sample, comprising: activating a measuring device; inserting a cartridge into the measuring device; placing a liquid sample into a well within the cartridge, the well comprising a well wall and a well floor, the well further comprising a disc, the disc comprising a first tracking point comprising a first color, the first tracking point proximate a rotational center of the disc, the disc also comprising a second tracking point comprising a second color spaced apart from the rotational center of the disc, the first color different from the second color, wherein the well floor is relatively hydrophilic, and the well wall is relatively hydrophobic with respect to the well floor; activating a magnetic field of the measuring device; rotating the disc in a first direction using the magnetic field; rotating the disc in a second direction opposite the first direction using the magnetic field; illuminating the disc; tracking the first tracking point and the second tracking point of the disc with a video camera; and calculating changes in movement of the second tracking point with respect to the first tracking point of the disc with a processor to determine coagulation parameters.

In some configurations, calculating changes in movement of the first tracking point and the second tracking point of the disc occurs in real time.

In some configurations, the magnetic field comprises a contactless magnetic coupling.

In some configurations, the method comprises displaying the coagulation parameters on a display.

In some configurations, the display is a smartphone display.

In some configurations, rotating the disc in a first direction comprises rotating the disc 4° 45' degrees over 10 seconds.

In some configurations, the method comprises controlling an internal temperature in the measuring device.

In some configurations, the disc further comprises a spindle, such that the disc is spaced apart from a floor of the well.

In some configurations, the disc comprises ferromagnetic material to facilitate rotating the disc in the first direction using the magnetic field.

In some configurations, tracking comprises tracking a reduction in motion of the second tracking point with respect to the first tracking point as the magnetic field becomes no longer strong enough to overcome viscoelasticity of the liquid sample as the liquid sample coagulates.

In some embodiments, a method for measuring coagulation of a sample, comprising: activating a measuring device; inserting a cartridge into the measuring device; placing a liquid sample into a well within the cartridge, the well comprising a well wall and a well floor, the well further comprising a disc, the disc comprising a first tracking point comprising a first color, the first tracking point proximate a rotational center of the disc, the disc also comprising a second tracking point comprising a second color spaced apart from the rotational center of the disc, the first color different from the second color, the disc spaced apart from a well floor via a spindle operably connected to the disc, wherein the well floor is relatively hydrophilic, and the well wall is relatively hydrophobic with respect to the well floor; controlling an internal temperature of the measuring device; activating a magnetic field of the measuring device; rotating the disc in a first direction using the magnetic field; rotating the disc in a second direction opposite the first direction using the magnetic field; illuminating the disc; tracking the first tracking point and the second tracking point of the disc with a camera; and calculating changes in movement of the second tracking point with respect to the first tracking point of the disc with a processor to determine coagulation parameters. In some embodiments, tracking comprises tracking a reduction in motion of the second tracking point with respect to the first tracking point over time as the magnetic field becomes no longer strong enough to overcome viscoelasticity of the liquid sample as the liquid sample coagulates.

In some configurations, the well floor comprises a hydrophilic coating.

In some configurations, the well wall comprises a hydrophobic coating.

In some configurations, the disc is positioned substantially parallel to the well floor.

In some configurations, a disc diameter to well diameter can be between about 0.5 and about 1.0.

In some configurations, a disc diameter to well diameter can be between about 0.6 and about 0.8.

In some configurations, a well diameter to well depth ratio is between about 3.0 and about 6.0.

In some configurations, a well diameter to well depth ratio is between about 4.0 and about 5.0.

In some configurations, the method comprising validating the cartridge by observing indicia associated with the cartridge.

In some configurations, the indicia comprises a QR code or barcode.

In some configurations, the indicia comprises an RFID tag.

In some configurations, the indicia comprises cross-hairs.

In some embodiments, a cartridge for measuring coagulation of a sample, comprises any number of: a well configured to hold a liquid sample, the well comprising a well wall and a well floor, the well further comprising a disc, the disc comprising a first tracking point comprising a first color, the first tracking point proximate a rotational center of the disc, the disc also comprising a second tracking point comprising a second color spaced apart from the rotational center of the disc, the first color different from the second color, the disc spaced apart from a well floor via a spindle operably connected to the disc, wherein the well floor is relatively hydrophilic, and the well wall is relatively hydrophobic with respect to the well floor.

In some configurations, the well floor comprises a hydrophilic coating.

In some configurations, the well wall comprises a hydrophobic coating.

In some configurations, the disc is positioned substantially parallel to the well floor.

In some configurations, a disc diameter to well diameter can be between about 0.5 and about 1.0.

In some configurations, a disc diameter to well diameter can be between about 0.6 and about 0.8.

In some configurations, a well diameter to well depth ratio is between about 3.0 and about 6.0.

In some configurations, a well diameter to well depth ratio is between about 4.0 and about 5.0.

In some embodiments, disclosed herein is a method for measuring coagulation of a liquid, comprising one or more of: activating a measuring device; controlling internal temperature in the measuring device; inserting a cartridge into the measuring device; injecting a liquid sample into a well within the cartridge, the well comprising a sidewall and a floor; providing a contactless magnetic coupling, reciprocating the well or a movable device within the well with the magnetic coupling over an angular sweep range; illuminating the movable device; observing the movable device with a video camera; recording times of changes in movement of the movable device; and adjusting the angular sweep range based at least in part on the recorded changes in movement of the movable device.

In some configurations, the reciprocating comprises reciprocating the movable device with a contactless magnetic coupling, and the recording comprises recording time differentiation between a start of movement of the movable device and slowing and stopping of movement of the movable device.

In some configurations, a method also includes placing the movable device in the well after the injecting of the liquid sample.

In some configurations, the turning on comprises connecting a power source to the heat controller and to a motor for the reciprocating, and starting the illuminating and a video camera and a central processor for recording times of changes in movement of the movable device and creating displays according to the changes in movement of the movable device.

In some configurations, starting the illuminating, the video camera and the central processor comprises turning on a smartphone connected to the measuring device.

In some configurations, adjusting the angular sweep range comprises adjusting the angular sweep range proportional to a recorded rotational sweep movement of the movable device at a point in time following initiation of reciprocating the well or the movable device.

In some configurations, adjusting the angular sweep range comprises adjusting the angular sweep range substantially equal to a recorded rotational sweep movement of the movable device.

In some configurations, adjusting the angular sweep range comprises adjusting the angular sweep range substantially equal to a recorded rotational sweep movement of the movable device.

In some configurations, controlling the internal temperature in the measuring device comprises synchronizing the internal temperature with a body temperature of a patient from which the liquid sample was obtained from.

In some configurations, illuminating the movable device comprises illuminating with LED light.

In some configurations, illuminating the movable device comprises illuminating with UV light.

In some configurations, the movable device comprises a disk.

In some configurations, the disk comprises ferrous metal.

In some configurations, the disk comprises a wire.

In some configurations, the wire comprises steel.

In some embodiments, a system for measuring coagulation of a liquid can include nay number of the following: a measuring device; a controller configured to regulate an internal temperature in the measuring device; a light source operably associated with the measuring device; a video camera; a cartridge comprising a well and a movable device, the cartridge configured to be inserted into a receptacle of the measuring device, the well configured to house a liquid sample therein; a magnetic actuator configured to reciprocate the well or a movable device within the well via a contactless magnetic coupling over an angular sweep range; wherein the video camera is configured to record times of changes in movement of the movable device; and wherein the controller is configured to regulate the magnetic actuator by adjusting the angular sweep range based at least in part on recorded changes in movement of the movable device.

In some configurations, adjusting the angular sweep range comprises adjusting the angular sweep range proportional to a recorded rotational sweep movement of the movable device at a point in time following initiation of reciprocating the well or the movable device.

In some configurations, adjusting the angular sweep range comprises adjusting the angular sweep range substantially equal to a recorded rotational sweep movement of the movable device.

In some configurations, adjusting the angular sweep range comprises adjusting the angular sweep range substantially equal to a recorded rotational sweep movement of the movable device.

In some configurations, the controller is configured to synchronize the internal temperature in the measuring device with a body temperature of a patient from which the liquid sample was obtained from.

In some configurations, the light source comprises an LED.

In some configurations, the light source comprises UV light.

Also disclosed herein is a method for measuring coagulation of a sample, comprising any number of: activating a measuring device; inserting a cartridge into the measuring device; placing a liquid sample into a well within the cartridge, the well comprising a well wall and a well floor, the well further comprising a disc, the disc comprising a first tracking point comprising a first color, the first tracking point proximate a rotational center of the disc, the disc also comprising a second tracking point comprising a second color spaced apart from the rotational center of the disc; activating a magnetic field of the measuring device; rotating the disc in a first direction using the magnetic field; rotating the disc in a second direction opposite the first direction using the magnetic field; illuminating the disc; tracking the first tracking point and the second tracking point of the disc with a video camera; and calculating changes in movement of the second tracking point with respect to the first tracking point of the disc with a processor to determine coagulation parameters, wherein tracking comprises identifying one or more of the color and shape of the first tracking point and the second tracking point.

In some configurations, identifying comprises identifying one or more of the hue, saturation, brightness, size, shape, convexity, and circularity of the first tracking point and the second tracking point.

In some configurations, calculating changes in movement comprises calculating changes in movement over a first period of time and a second period of time, and weighting changes in movement over a first period of time differently from changes in movement over a second period of time.

In some configurations, calculating changes in movement of the first tracking point and the second tracking point of the disc occurs in real time.

In some configurations, the magnetic field comprises a contactless magnetic coupling.

In some configurations, a method further comprises displaying the coagulation parameters on a display.

In some configurations, the display is a smartphone display.

In some configurations, a method also comprises controlling an internal temperature in the measuring device.

In some configurations, the disc comprises ferromagnetic material to facilitate rotating the disc in the first direction using the magnetic field.

In some configurations, tracking comprises tracking a reduction in motion of the second tracking point with respect to the first tracking point as the magnetic field becomes no longer strong enough to overcome viscoelasticity of the liquid sample as the liquid sample coagulates.

In some configurations, a method for measuring coagulation of a sample comprises any number of the following: activating a measuring device; inserting a cartridge into the measuring device; placing a first liquid sample into a first well within the cartridge, the first well further comprising a first disc, the first disc comprising a first tracking point comprising a first color, the first tracking point proximate a rotational center of the first disc, the first disc also comprising a second tracking point comprising a second color spaced apart from the rotational center of the disc, the first color different from the second color, the disc spaced apart from a well floor via a spindle operably connected to the disc; placing a second liquid sample into a second well within the cartridge, the second well further comprising a second disc, the second well being concentric with respect to the first well and spaced radially outward from the first well, the second disc comprising a third tracking point comprising a third color, controlling an internal temperature of the measuring device; activating a magnetic field of the measuring device; rotating the first disc and the second disc in a first direction using the magnetic field; rotating the first disc and the second disc in a second direction opposite the first direction using the magnetic field; illuminating the first disc and the second disc; tracking the first tracking point, second tracking point, and third tracking point of the disc with a camera; and calculating changes in movement of the second tracking point and/or the third tracking point with respect to the first tracking point of the disc with a processor to determine coagulation parameters, wherein tracking comprises tracking a reduction in motion of the second tracking point and/or the third tracking point with respect to the first tracking point over time.

In some embodiments, disclosed herein is a cartridge for measuring a parameter of a plurality of liquid samples, comprising: a first well within the cartridge, the first well further comprising a first disc, the first disc comprising a first tracking point comprising a first color, the first tracking point proximate a rotational center of the first disc, the first disc also comprising a second tracking point comprising a second color spaced apart from the rotational center of the disc, the first color different from the second color, the disc spaced apart from a well floor via a spindle operably connected to the disc; and a second well within the cartridge, the second well further comprising a second disc, the second well being concentric with respect to the first well and spaced radially outward from the first well, the second disc comprising a third tracking point comprising a third color.

In some embodiments, a system for measuring a biological parameter (including but not limited to coagulation) can include any number of features as disclosed herein.

In some embodiments, a removable cartridge for measuring a biological parameter (including but not limited to coagulation) can include any number of features as disclosed herein.

In some embodiments, a method for measuring a biological parameter (including but not limited to coagulation) can include any number of features as disclosed herein.

These and further and other objects and features of some embodiments of the invention are apparent in the disclosure, which includes the above and ongoing written specification, with the claims and the drawings.

BRIEF DESCRIPTION OF THE DRAWINGS

FIG. 1G is an image describing BioMEMS device marking relative to tracking from a second reference point, according to some embodiments.

FIG. 2A are images describing translation of device motion into zero amplitude profile, according to some embodiments.

FIGS. 11A-15 show examples of cartridges, according to some embodiments.

FIGS. 11A and 11B are perspective and a schematic side view showing an example of a cartridge, platform, well, extended lid, an abutment on the platform and a disk attached to the lid, all of which are inserted in a receiver before fluid is injected into the well, according to some embodiments.

FIG. 14 is a perspective view of a cartridge without a lid showing a fluid injection port at one end of a passageway to the well and a retaining clip for retaining the cartridge in the receiver, according to some embodiments.

FIG. 15 shows a two-piece injection construction of the cartridge platform for compatibility with manufacture by injection molding, according to some embodiments.

FIGS. 19-30D disclose additional embodiments relating to medical analyzers and removable cartridges.

DETAILED DESCRIPTION

Figure 1A:
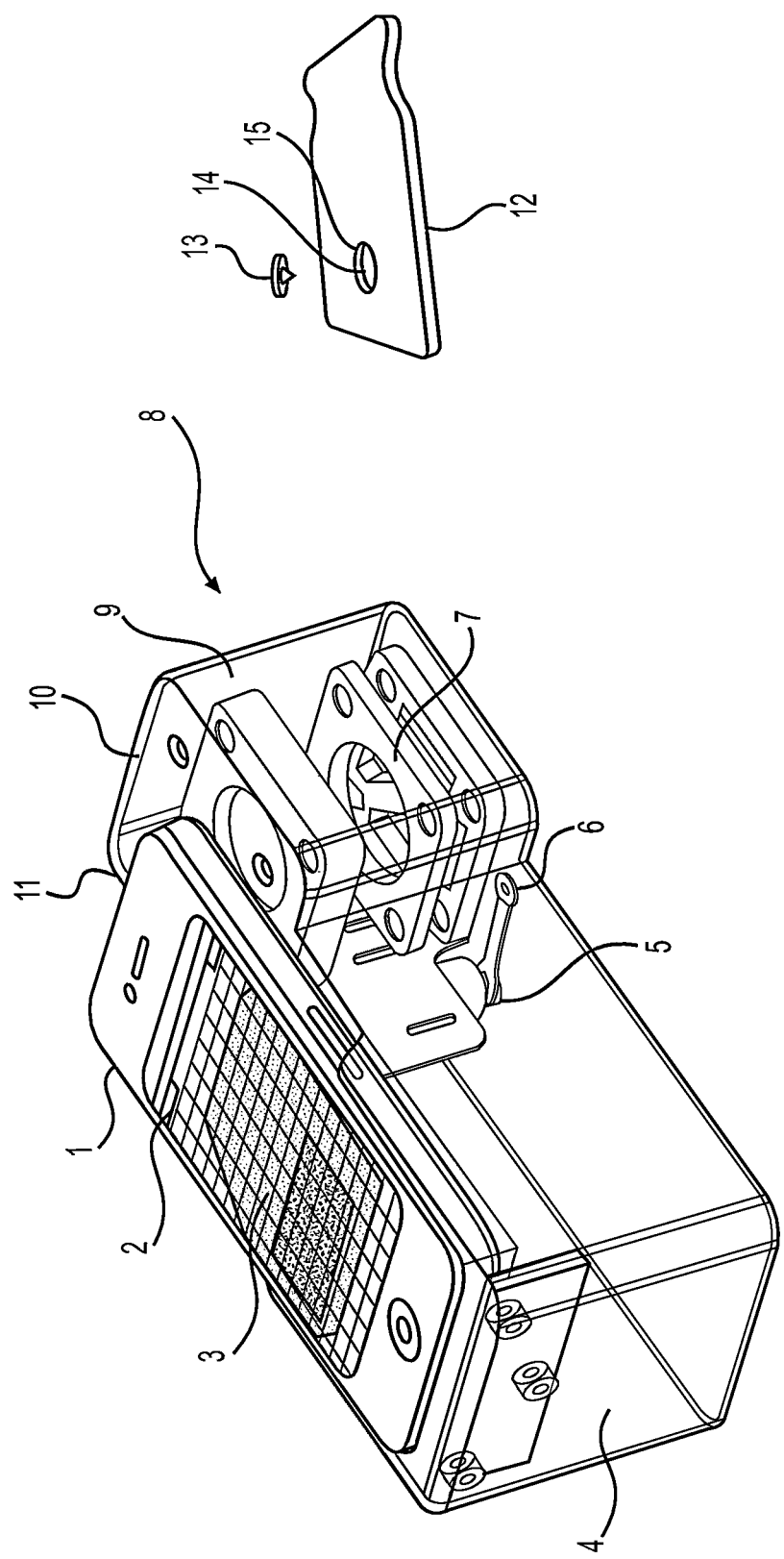
FIG. 1A is a CAD rendering of an embodiment of a Coagulation Profiler and subsystems.

The invention provides, in some aspects, a handheld medical analyzer platform and biological microelectromechanical systems (BioMEMS) cartridges. This combined system uses microfluidics, optics, a mobile device (e.g. a smartphone or tablet) and video analysis software to create a handheld analyzer that produces data used in medical and biological diagnostics. In this embodiment, two primary components are the handheld medical analyzer and the coagulation profile cartridge. The combination of the handheld analyzer and coagulation profile cartridge can provide results equal to bench top systems used in hospitals, such as TEG and ROTEM. The handheld medical analyzer is a platform that is capable of analyzing a variety of cartridges. However, the coagulation profile cartridge may be specific to coagulopathy applications only.

Although the cartridges are intended to be disposable, they also can be implemented in a permanent fashion when cleaned properly and constructed of the proper material. Combined, the handheld medical analyzer and coagulation profile cartridge produce a coagulation profile which is displayed and stored on the analyzer. In some embodiments of the invention, the cartridge provides data used in diagnosing different forms of coagulopathy.

Although the combination of the handheld analyzer and coagulation profile cartridge is one part of certain embodiments of the invention, the handheld analyzer is not limited to analyzing this specific cartridge.

Other similar embodiments include profiling the coagulation of Limulus amebocyte lysate (LAL) or other analytes. In this case the extent of LAL coagulation would be representative of the presence of gram negative bacteria, since the LAL reacts with bacterial endotoxin or lipopolysaccharide (LPS).

A similar cartridge would also apply to other assays that detect a physical change in the sample, such a viscosity, elasticity or viscoelasticity. Examples of these embodiments may include saliva, cervical mucus or other body fluids.

Furthermore the handheld analyzer is also capable of using the same basic configuration to analyze a great many cartridges. These embodiments could also capture data using the video camera and interrogated using the CPU and GPU running software. These cartridges include, but are not limited to CBC, HTC, $PaO_2$, pH and blood type.

Likewise similar use of a smartphone for cartridge analysis is not limited to video input, but also could use many other sensors on the smartphone, including direct electrical signals, wireless signals, manometers, accelerometers, gyroscopes and compasses. This includes combinations of the different methods of obtaining direct sensor information and indirect supplementary sensor information. An example of this would be using the combined system to provide a coagulation profile, while using the smartphone, wireless communication, accelerometers, gyroscopes, GPS, etc. to provide stabilization in rough environments such as a helicopter which is in motion and vibrating. These subsystems could also be used to send the coagulation profile, GPS coordinates to the ER providing an estimated time of arrival (ETA) and allowing for preparation of blood products, etc., in advanced for the patient's arrival.

One embodiment is shown in FIG. 1A. The coagulation profile cartridge 12 is inserted into the cartridge slot 7 where the BioMEMS device motion interfaces with the sample 15 and the motion is captured using the smartphone 1 video camera 11 and is analyzed using the smartphone central processing unit (CPU), graphics processor unit (GPU) running software configured to track and analyze the desired motion. The resultant coagulation profile 3 is displayed 2 on smartphone 1 (e.g. iPhone) screen along with the measured parameters, similar to TEG/ROTEM, Table 1, Table 2. A custom enclosure 4 provides a docking point for the smartphone and attachment of peripheral components. In this embodiment the peripheral components consist of a motor 5, mechanical linkage 6 and compact microscope assembly 8, light source 9 and temperature control unit 10. The motor and linkage can be replaced with a servo and gearing, to provide the desired rotational actuation.

The coagulation profile cartridge 12 is interrogated using the compact microscope 8 and video camera 11.

Figure 1B:
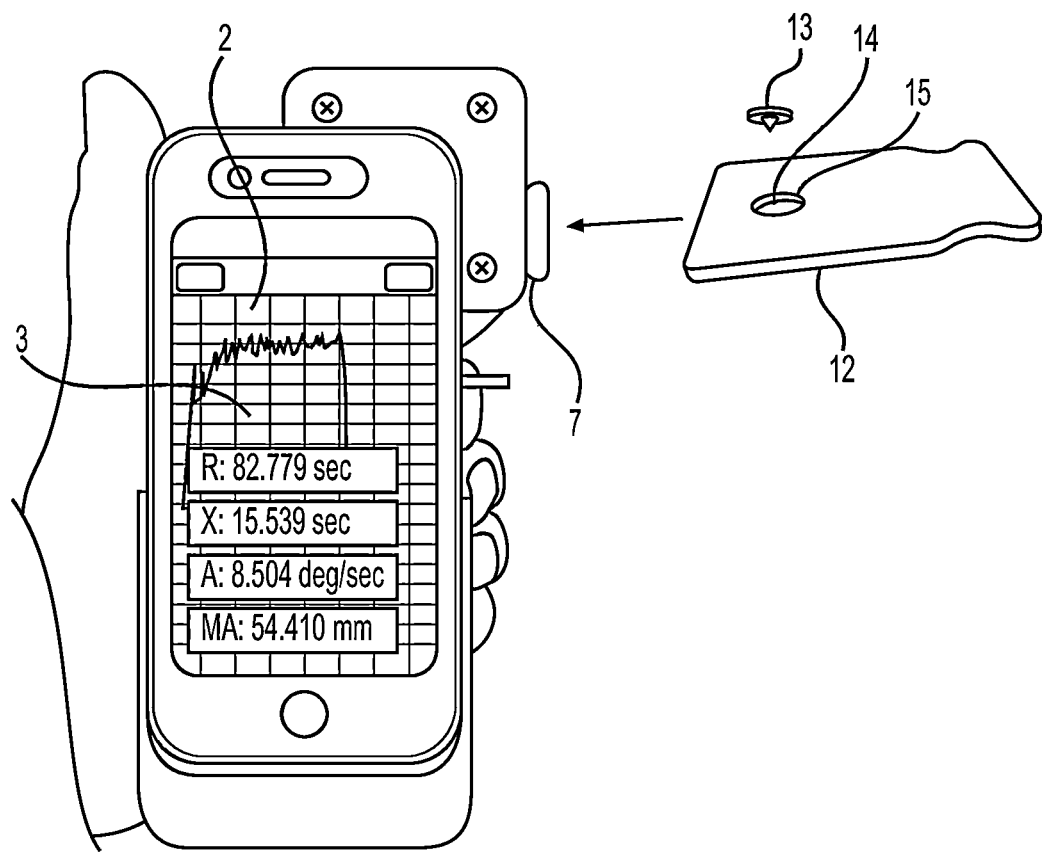
FIG. 1B is an embodiment showing blood placed on cartridge is loaded into the analysis slot.

The loading protocol for the simplest embodiment of the combined system is: place blood 15 into well 14 on cartridge 12 and load the cartridge into analysis slot 7, also shown in FIG. 1B.

The disc 13 may be removed prior to filling the well 14, or the well may be filled with the disc in place. In this simple embodiment the well would be filled using a pipette.

Figure 1C:
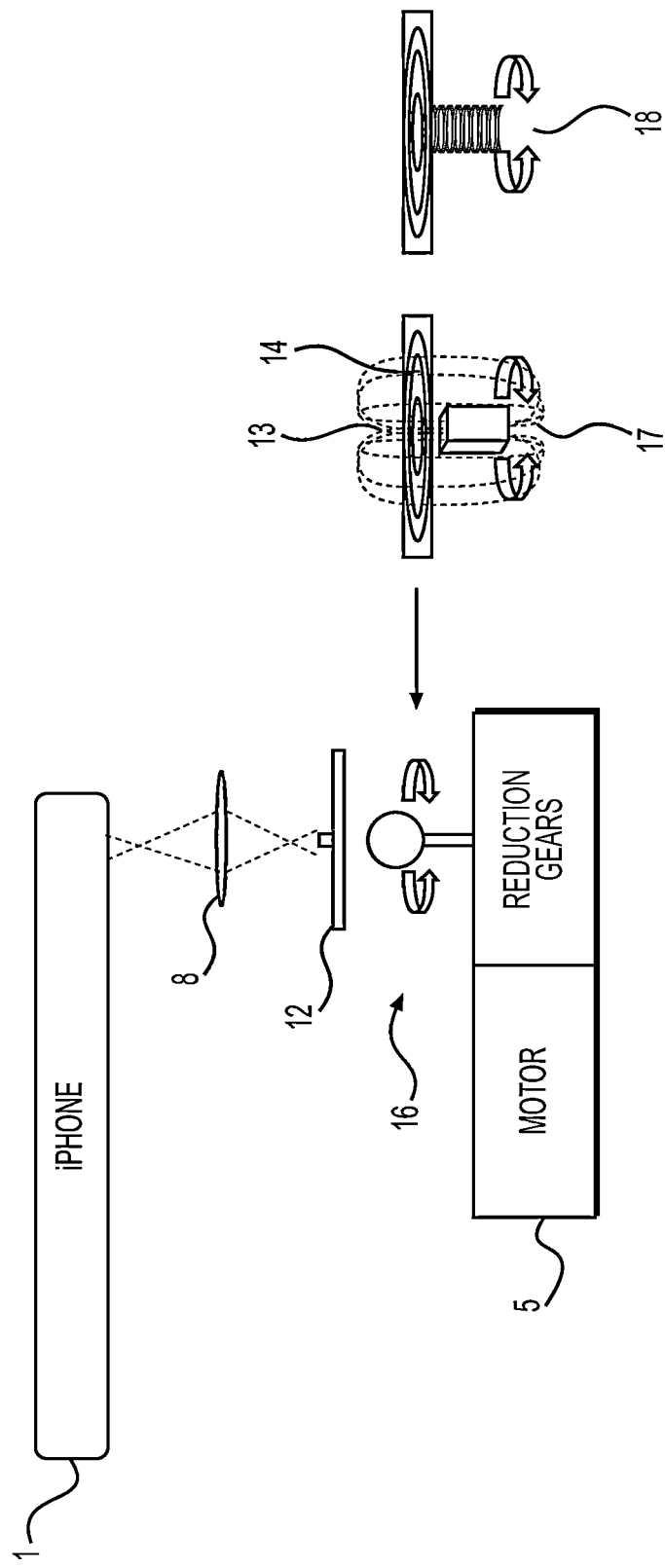
FIG. 1C is a schematic of an embodiment of cartridge actuation and sub system.

Upon loading the cartridge the measurement begins as the disk is actuated, as shown in FIG. 1C. Actuation in this embodiment is performed using a motor 5, mechanical linkage 6 in the form of reduction gears and magnet 16, which couples motion to the cartridge disc 13. Other embodiments would include electromagnetic induction or direct mechanical drive via a spring.

By embedding ferrous metal into the cartridge disc 13, the magnetic field 17 couples the disc with the magnet. This coupling forms a link analogous to a torsion spring 18. Motion is thereby induced into the disc by rotating the magnet. In this embodiment the rotation is ±4° 45' degrees over 10 seconds. Other embodiments would include any number variations in the angular rotation over time.

Figure 1D:
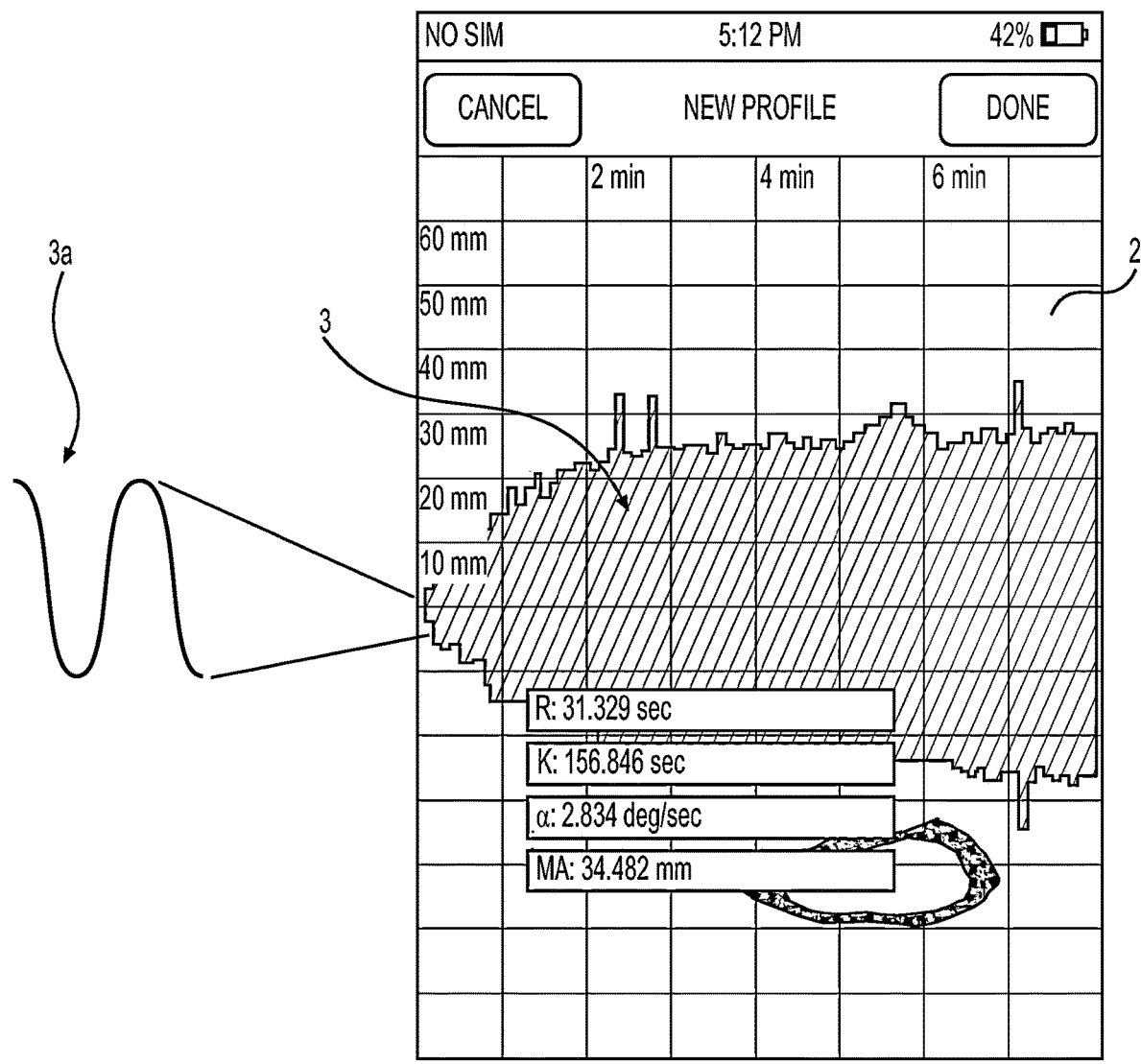
FIG. 1D is a description of displayed profile, relative to cartridge actuation, according to some embodiments.

In the embodiment the degree to which the motion is decoupled is representative of the displayed 2 profile 3, as shown in FIG. 1D. Both processed profiles 3 and preprocessed traces are sinusoidal waveforms, e.g. 3a, that represent the motion or decoupled motion. The sinusoidal waveform is acquired using the video camera and the CPU and GPU running software configured to capture and analyze the sample motion.

Figure 1E:
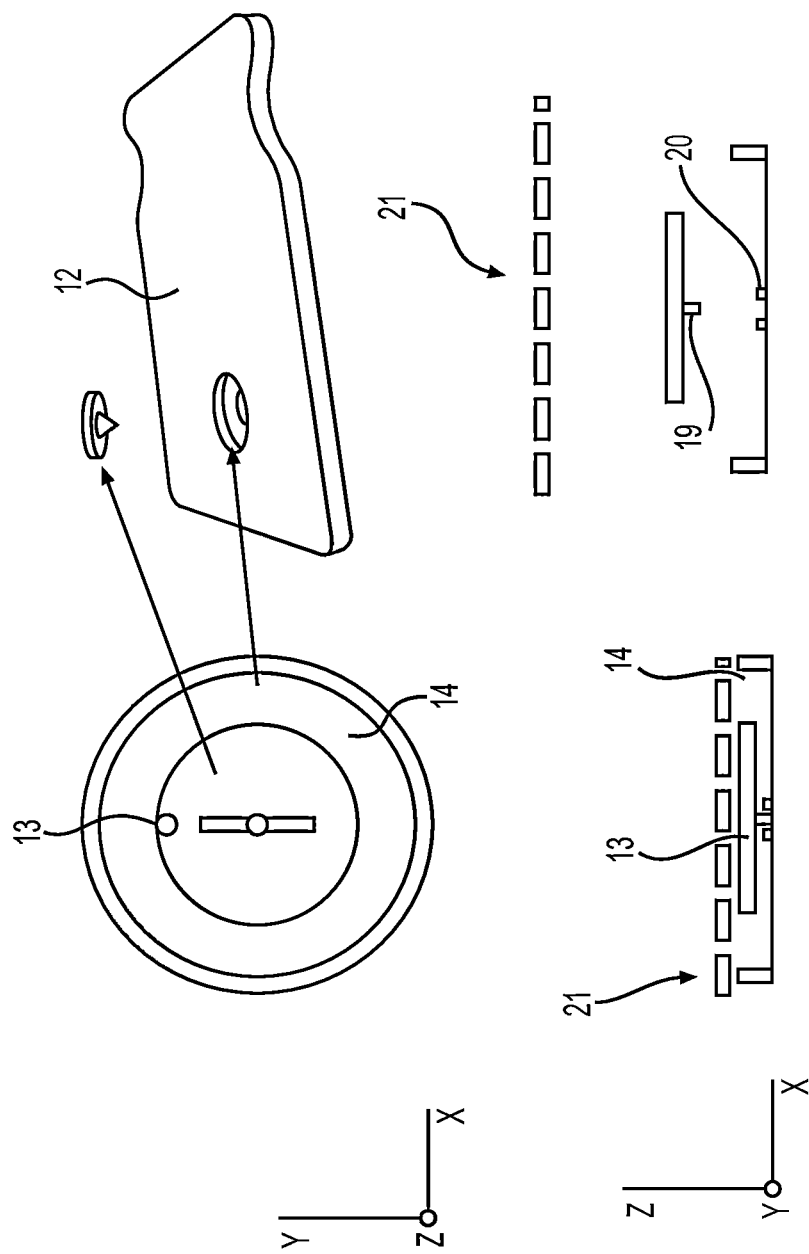
FIG. 1E is a detailed description of a BioMEMS coagulation profile cartridge, according to some embodiments.

The alpha numeric displays, as one non-limiting example:
R: 31.329 sec
K: 156.846 sec
a: 2.834 deg/sec
MA: 34.482 mm FIG. 1E shows a cartridge 12, an enlarged well top view, side cross section and an exploded side cross section. As shown in FIG. 1E, the cartridge has a well 14 and a disc 13. The disc is seated in the well via a spindle 19 and a bearing cup 20, at the bottom of the well. Both the well and the disc are sealed in the cartridge with a clear plastic lid 21. The lid can be hinged, sliding to allow sample insertion, or a microfluidic channel may be used to load the sample into the well. This particular subcomponent of the cartridge may be realized in a number of different embodiments. These range from a simple hole in the lid to more complex automated microfluidics channels and chambers which meter the appropriate amount of blood or other sample, and/or reagent into the well. Likewise the insertion of the sample may range from manually using a pipette to the use of automated microfluidics.

Figure 1F:
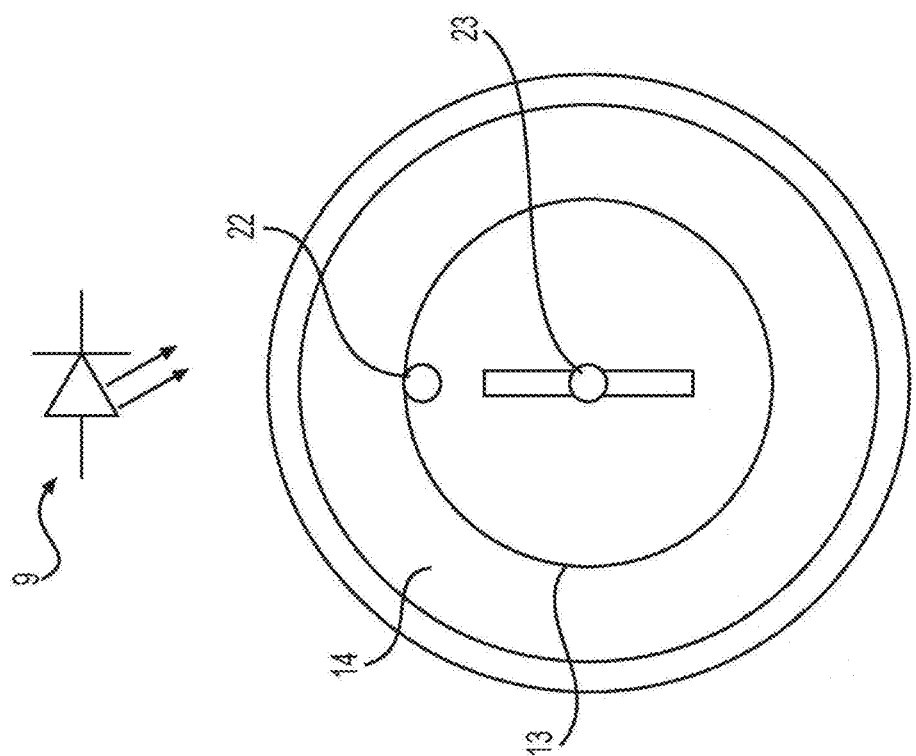
FIG. 1F is an image describing BioMEMS device marking relative to tracking, according to some embodiments.

The motion of the disc is captured by tracking two points overtime. FIG. 1F shows the pivot point 23 at the center of the disc 13 and a tracking point 22 at the outside edge of the disc. Each point is a unique color. In this embodiment the colors are florescent when illuminated using a UV LED light source 9. Both points are tracked by selecting the color to be tracked on the smartphone screen followed by selecting a threshold for the hues of the selected color to be included. The centroid of each of the prescribed points is then calculated to determine the exact location to be tracked. The angular motion is then calculated by comparing the centroid of the pivot point 23 to the centroid of the tracking point 22. This calculation can be performed real-time and is used to calculate the displayed profile continuously over time.

FIG. 1F shows a disk with both a tracking point and pivot point on the disk. By tracking the angular motion of the tracking point relative to the pivot point the angular motion can be calculated. In another embodiment (FIG. 1G) the motion can be calculated from a second tracking point well reference point 1. The relative motion can be calculated between the tracking point and the well edge reference point. When using the embodiment shown in FIG. 1F the embodiment is more impervious to motion since the tracking point and the pivot point are on the same disk. In the embodiment using a reference point on the well edge FIG. 1G, unintended motion between the tracking point and well reference point 1 will register as interference or noise.

In some embodiments, color and shape can be used to track the tracking point and the pivot point. In some embodiments, an algorithm can utilize one, two, or more of hue, saturation, brightness, size, shape, convexity, and/or circularity. This can be sufficient in most cases, however there are multiple variations of the orientation of the disk in the well and as the disk moves, these parameters sometimes change throughout the motion. Likewise there are sometimes reflections from the LEDs that can cause it to lose track. In some embodiments, reducing the reflections and color variation can be achieved by using UV LEDs that create a better contrast between the tracking points and the background. Likewise, decals that have a black background can be used further increasing the contrast between the tracking points and the background. Furthermore, machine vision tracking techniques can be incorporated to include machine learning.

In some embodiments, distinguishing two tracking points can be realized with the following algorithm, with the baseline represented by the variable B, the subsequent motion trace represented by the variable S and the displayed amplitude is represented by A:

$$(1-(B/S))*75 \text{ mm}=A$$

$$(1-(40/50))*75 \text{ mm}=15 \text{ mm} \qquad \text{Example:}$$

In another embodiment, rather than using a constant angular sweep, the sweep changes to optimize sensitivity of the different phases of coagulation and maintain a preferred torque profile.

In some embodiments, the rotation starts sweeping a large angular motion, e.g., about 50 degrees. As coagulation starts the system, e.g., a sensor observes a reduction in angular degree of induced motion, e.g. 10 degrees. This sensed reduction can be communicated to a controller which then reduces, in real-time or near real-time the amount of rotation of the magnet by 10 degrees to maintain a constant/near constant induced torque profile.

One non-limiting example of this is when a disk is rotated over 50 degrees sweep in total. As the blood coagulates the induced motion decreases, such as, for example, from 50 degrees to 40 degrees. This is observed by the camera and algorithm and in turn the servo is adjusted to sweep to the lower angular measurement, e.g., 40 degrees. The algorithm also can adjust the number used in the subtraction algorithm that started with the baseline, e.g., of 45 degrees. As the coagulation continues the observed sweep is adjusted to reduce based on the last sweep. This continues until the maximum sweep is about 9 degrees or more, or about or at least about 6, 7, 8, 9, 10, 11, 12, 13, 14, 15, 16, 17, 18, 19, or 20 degrees, or ranges including any two of the foregoing values.

This can allow a greater sweep early on in the coagulation profile and a change in coagulation is more easily detected since it is inducing a larger change in the sweep. This also makes the system less susceptible to outside induced motion, since any motion induced will be less in comparison to the amount of motion being detected. This may not be true if one starts with a small rotation where a small amount of change is anticipated to be detected. Any relatively small induced motion from outside will be more pronounced since the motion being detected is on the order of the potential noise. With no change, using a large sweep decreases sensitivity at the end of the coagulation phase where the residual motion is very small and the difference between normal and abnormal may only be one degree or even less. This algorithm advantageously allows this late motion to be weighted differently than early motion and the result helps increase sensitivity upon the final stage of viscoelastic testing.

Example of Large Sweep with No Correction

| S | B | S/B | 1 − S/B | A |
|---|---|---|---|---|
| 40.0 | 50.0 | 0.8 | 0.2 | 15.0 |
| 30.0 | 50.0 | 0.6 | 0.4 | 30.0 |
| 20.0 | 50.0 | 0.4 | 0.6 | 45.0 |
| 10.0 | 50.0 | 0.2 | 0.8 | 60.0 |
| 5.0 | 50.0 | 0.1 | 0.9 | 67.5 |
| 2.0 | 50.0 | 0.0 | 1.0 | 72.0 |

Example of Controlled Reduction of B Relative to S

| S | B | S/B | 1 − S/B | A |
|---|---|---|---|---|
| 40.0 | 50.0 | 0.8 | 0.2 | 15.0 |
| 30.0 | 40.0 | 0.8 | 0.3 | 18.8 |
| 20.0 | 30.0 | 0.7 | 0.3 | 25.0 |
| 10.0 | 30.0 | 0.3 | 0.7 | 50.0 |
| 5.0 | 20.0 | 0.3 | 0.8 | 56.3 |
| 2.0 | 10.0 | 0.2 | 0.8 | 60.0 |

In some embodiments, methods can be implemented without controlling the servo. In this case the sensitivity would be augmented in software only.

Figure 2B:
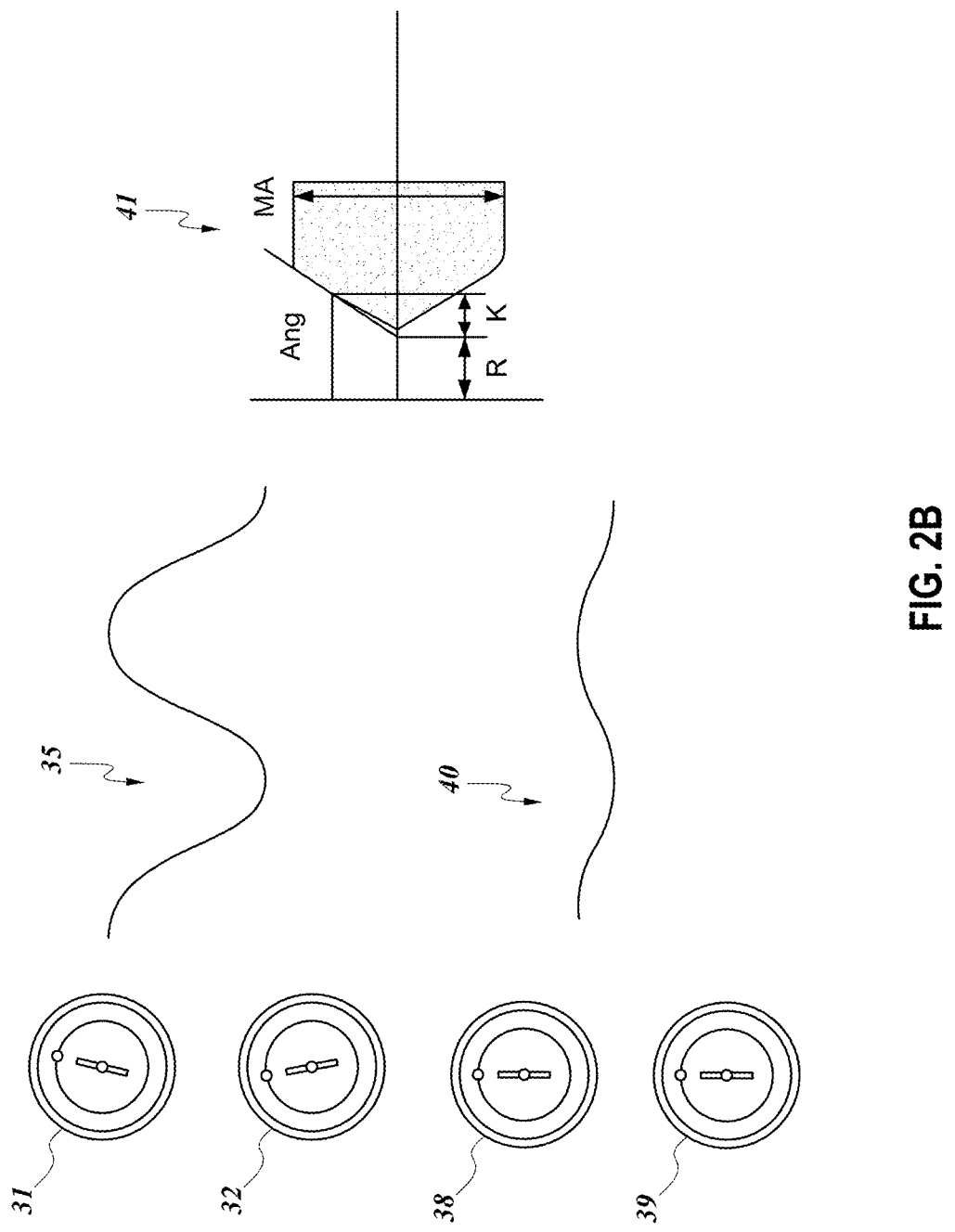
FIG. 2B are images describing translation of device motion into max amplitude (MA) profile, according to some embodiments.

The detailed translation of the device motion is shown in FIG. 2A. At the beginning of the measurement the disc motion is uninhibited and rotates the full range of motion, plus 4° 45' 31 and minus 4° 45' 32, in the fluid tested. This initial motion, before the onset of coagulation, is recorded as the baseline trace 35. The baseline trace is then differenced with the subsequent motion trace 36 to detect coagulation, which inhibits the coupling of motion of the magnet with the motion of the disc. In this embodiment, the displayed trace 37 (coagulation profile) is the difference between the baseline trace 35 and the subsequent motion trace 36. Prior to coagulation the baseline trace 35 is the same as the pre coagulation subsequent motion trace 36, and the coagulation profile 37 is the difference between the two: zero. As the blood coagulates, the induced motion is decoupled, and the magnetic field is no longer strong enough to overcome the viscoelasticity of the blood, as shown in FIG. 2B. Initially the motion is uninhibited 31, 32 producing the baseline motion 35. When coagulation occurs, decoupling reduces the induced motion 38, 39. Upon coagulation the large baseline trace 35 is differenced with the small post coagulation subsequent motion trace 40, resulting in a large amplitude profile 41. The moment in time shown, is at maximum amplitude represented by the parameter similar to the TEG parameter MA. As shown at the right of FIG. 2B and in FIG. 1B, the "reaction time" is the calculated time in decimal fractions of a second for a clot to reach 2 mm, "22 mm time" is the time in decimal fractions of a second for a clot to reach 22 mm, and "angle" is the slope of the angle between "reaction time" and 22 mm time. The "max clot" is maximum strength of a clot indicated in mm.

Figure 3:
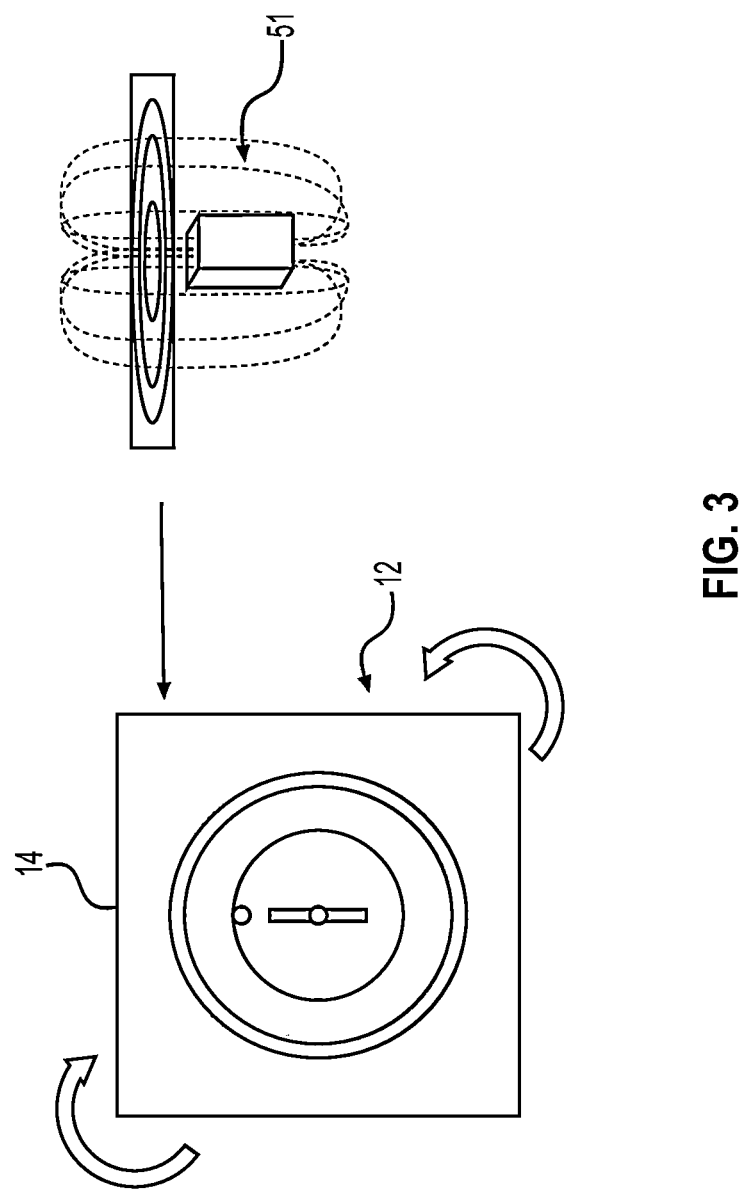
FIG. 3 shows an alternate embodiment with a fixed magnet, according to some embodiments.

A second embodiment of the BioMEMS device is shown in FIG. 3. In this embodiment a fixed magnet 51 is coupled to the disc. In this fixed magnet case, the rotation would be induced by rotating the cartridge 12 or well 14 within the cartridge. In this fixed magnet embodiment, the motion induced to the disc would be traced directly, with no differencing necessary. In this case the tracked motion could be directly used as the profile trace. Prior to the onset of coagulation there would be no motion coupled and the disc would oscillate uninhibited within the well. With no motion induced, the coagulation profile would be zero. In the fixed magnet case as the coagulation increases, the coupling would increase inducing more motion as coagulation continues. At MA the maximum amount of motion would be induced through the magnet.

Figure 4:
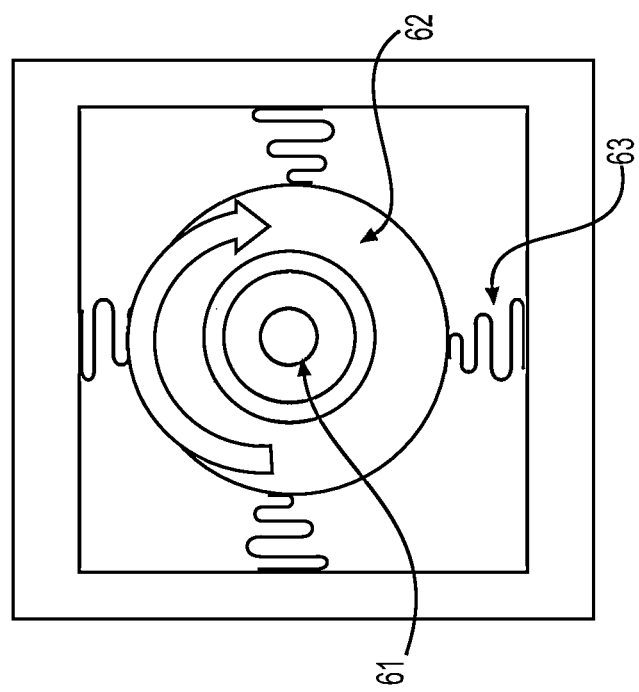
FIG. 4 shows an alternate embodiment with torsion springs, according to some embodiments.

A third embodiment of a coagulation profiling BioMEMS device is shown FIG. 4. This device has a center disc 61 and an outer ring 62 that is suspended by torsion springs 63. As the blood begins to coagulate, the rotating inner disc 61, actuated via an oscillating magnet, couples to the outer ring 62. This couples a reciprocating motion to the outer ring 2. At MA the maximum amount of motion would be induced through the magnet.

The BioMEMS embodiments shown are not all of the possible variations. For instance, one embodiment could use a disc fixed to the center of the well and actuate a ferrous ring in the well.

The measurement provided by some embodiments of the invention is impervious to motion. Due to the extremely small dimensions of the BioMEMS device in some cases, compared to the conventional size of TEG and ROTEM, the measurement is highly impervious to motion. The small mass of the device and small volume residing in the well present less inertia when external motion is applied. The ability to produce a noise-free measurement in the presence of motion is further enhanced by the magnetic coupling, which fixes the disc and the well in the magnetic field. Likewise the tracking points both being on the disk can reduce motion susceptibility compared to using a reference point external to the disk, such as referencing the edge of the well for relative motion.

Figure 5:
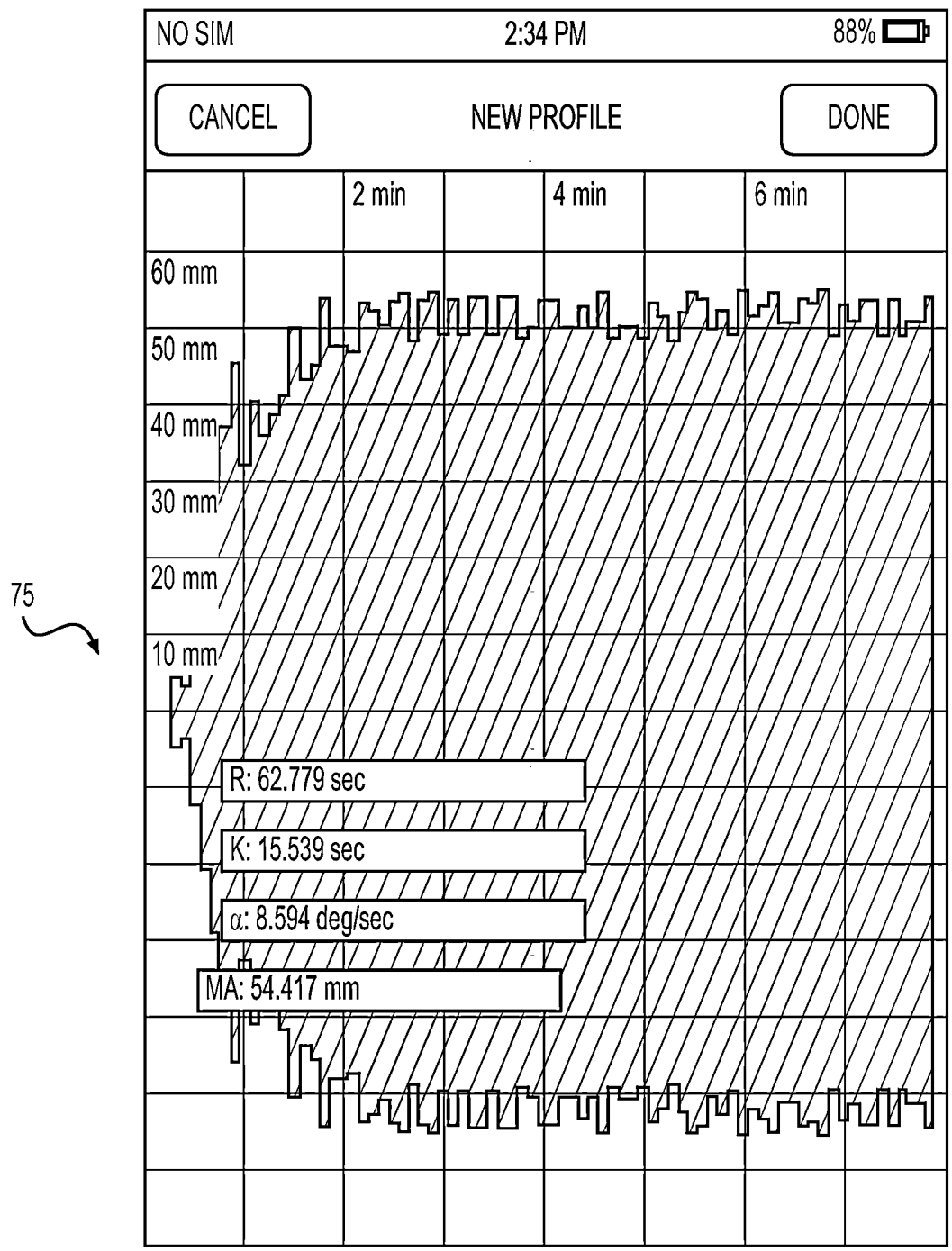
FIG. 5 is an image of a prototype showing accuracy of Level I control fluid, according to some embodiments.
Figure 6:
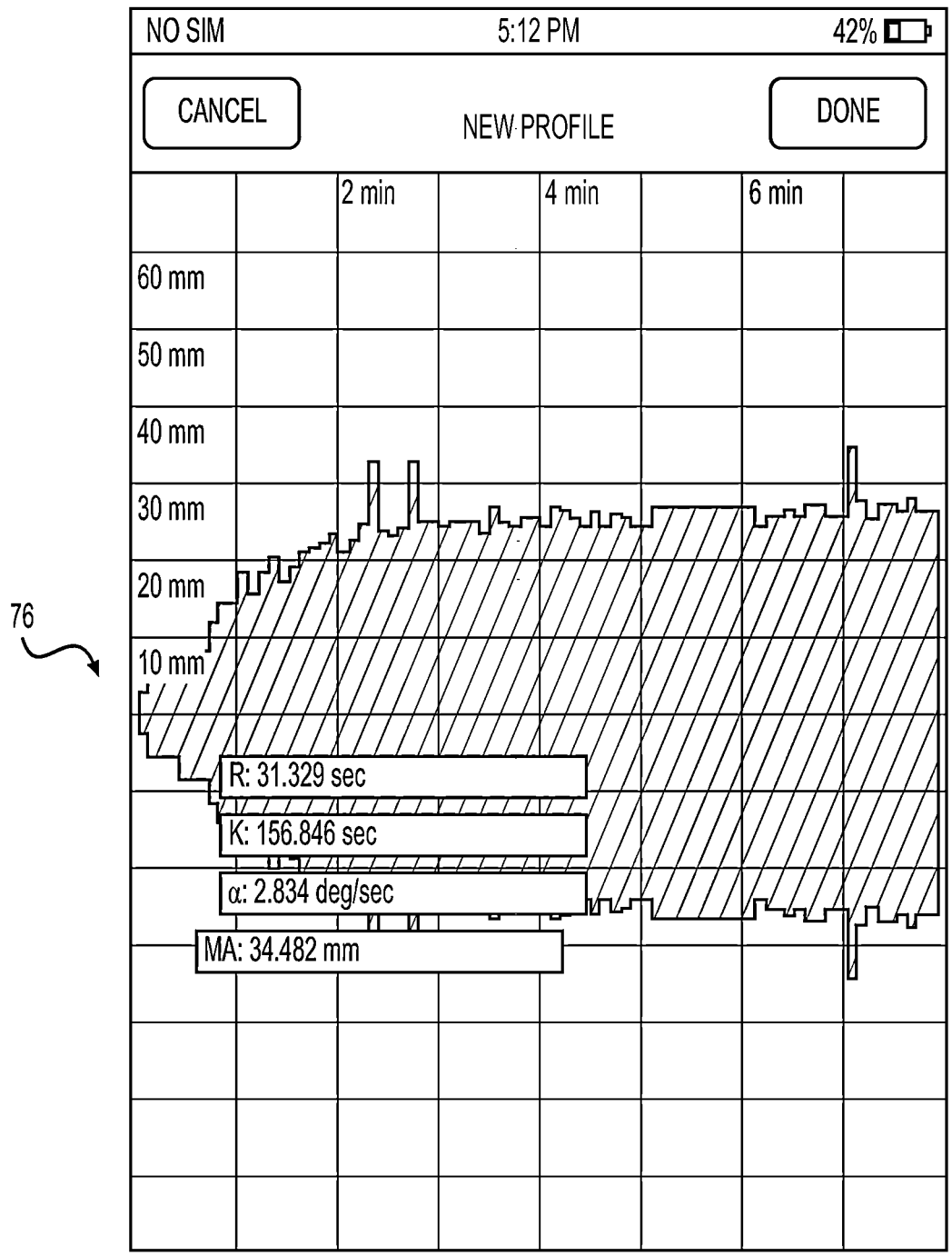
FIG. 6 is an image of a prototype showing accuracy of Level II control fluid, according to some embodiments.
Figure 7:
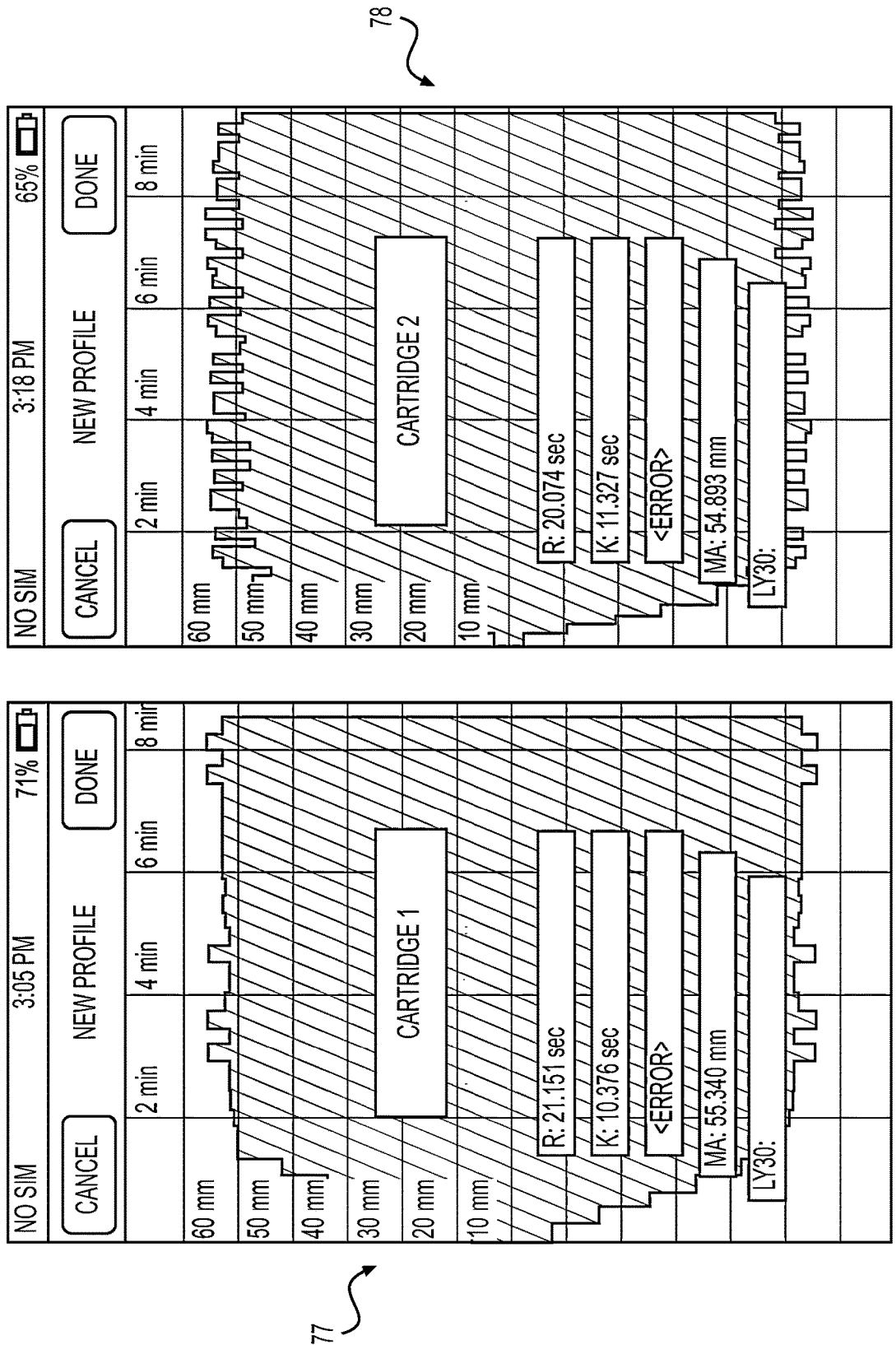
FIG. 7 is an image of a prototype showing repeatability of Level I profiles using two separate cartridges, according to some embodiments.
Figure 8:
FIG. 8 is an SEM image showing fibrin adhesion into surface of HDDA.

A prototype of an embodiment of the invention has provided concept validation. The image shown in FIG. 1B is an actual working prototype. The coagulation profile on the screen was taken using the prototype and shows the coagulation profile of using a quality control standard used and provided by Haemoscope, the makers of the TEG. A prototype of some embodiments of the invention has accurately differentiated between the Haemoscope Level 1 control (normal profile) as shown in screen 75 in FIG. 5 and the Level II control (abnormal profile) as shown on screen in FIG. 6. In addition repeatability has been demonstrated with multiple cartridges accurately measuring the samples with nearly identical results, as shown on screens 77 and 78 in FIG. 7. The polymer selection provides improved fibrin adhesion. The use of polymers for the fabrication of the cartridges has also been demonstrated to work well. In addition to being disposable and inexpensive to manufacture, the polymers have demonstrated advantages for us in some embodiments of this invention. Specifically, the use of HDDA promotes fibrinogen to be embedded into the polymer surface prior to the formation of fibrinogen. As the fibrinogen polymerizes it forms an excellent bond to the surfaces. This provides an ideal surface for detecting the viscoelasticity of the coagulating blood between the two HDDA surfaces. FIG. 8 shows fibrin 81 embedded into the surface of a HDDA disc sidewall. FIG. 8 also shows fibrin on the surface of the glass substrate, where air pockets are forming due to a lack of adhesion with no apparent fibrin embedded into the glass surface.

Figure 9:
FIG. 9 shows a forward surgical team attending a soldier, according to some embodiments.

FIG. 9 shows a forward surgical team attending a soldier at a forward position where some embodiments of the present invention is needed, a similar case would be an EMT or paramedic attending a trauma victim.

Figure 10A:
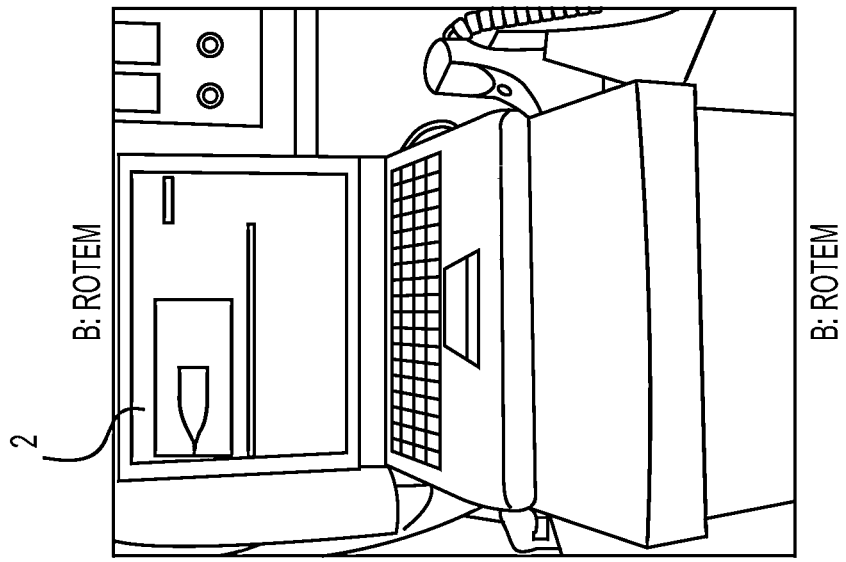
FIGS. 10A and 10B show prior art TEG and ROTEM devices.
Figure 10B:
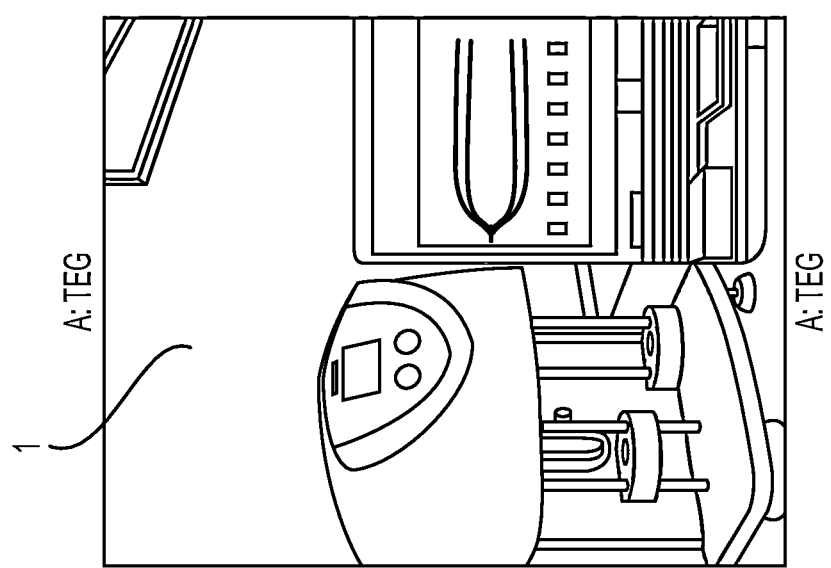

FIGS. 10A and 10B show prior art TEG and ROTEM devices.

FIGS. 11A and 11B are perspective and a schematic side view showing additional features of the cartridge 100, a platform 102, a well 104, an extended lid 106, an abutment 108 on the platform and a disk 110 attached to the lid 108, all of which are inserted in a receiver before fluid is injected into the well 104. FIG. 11B is a schematic representation of the well 104 and the disk 110 which is attached to a bottom of the lid 106.

Figure 12B:
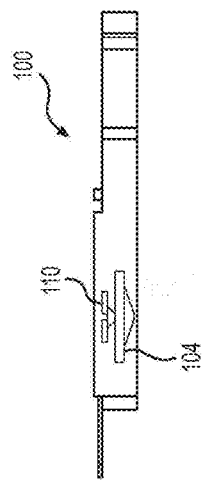
FIGS. 12A and 12B are perspective and a schematic side view showing a cartridge, platform, well, extended lid, an abutment on the platform and a disk attached to the lid. Moving the lid drops the disk into the well after fluid is injected into the well, according to some embodiments.
Figure 12A:
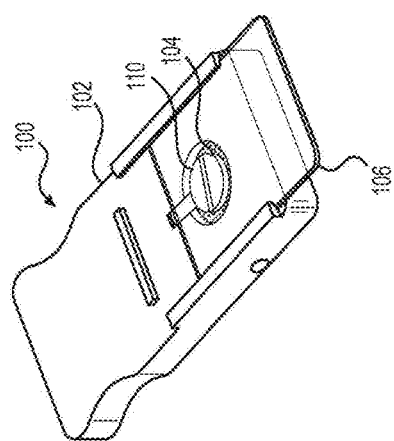

FIGS. 12A and 12B are perspective and a schematic side view showing disk loading technique of the cartridge 100, platform 102, the well 104, the extended lid 106, and an abutment 108 on the platform. Disk 110 is still attached to the lid 106.

Figure 13B:
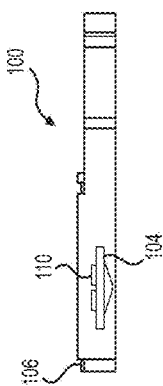
FIGS. 13A and 13B are perspective and a schematic side view showing a cartridge, platform, well, extended cover or lid, an abutment on the platform and a disk attached to the lid, all of which are inserted in a receiver before fluid is injected into the well. After fluid is injected, the lid is pushed back and the disk is dropped from the lid into the well, according to some embodiments.
Figure 13A:
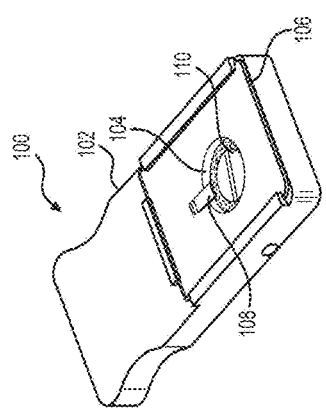

FIGS. 13A and 13B are perspective and a schematic side view showing a cartridge 100, the platform 102, well 104 and lid 106. An abutment 108 on the platform 102 has dislodged disk 110 from the lid after fluid is injected into the well and after lid 106 is pushed back and disk 110 is dislodged and dropped from the lid into the well.

Figure 14:
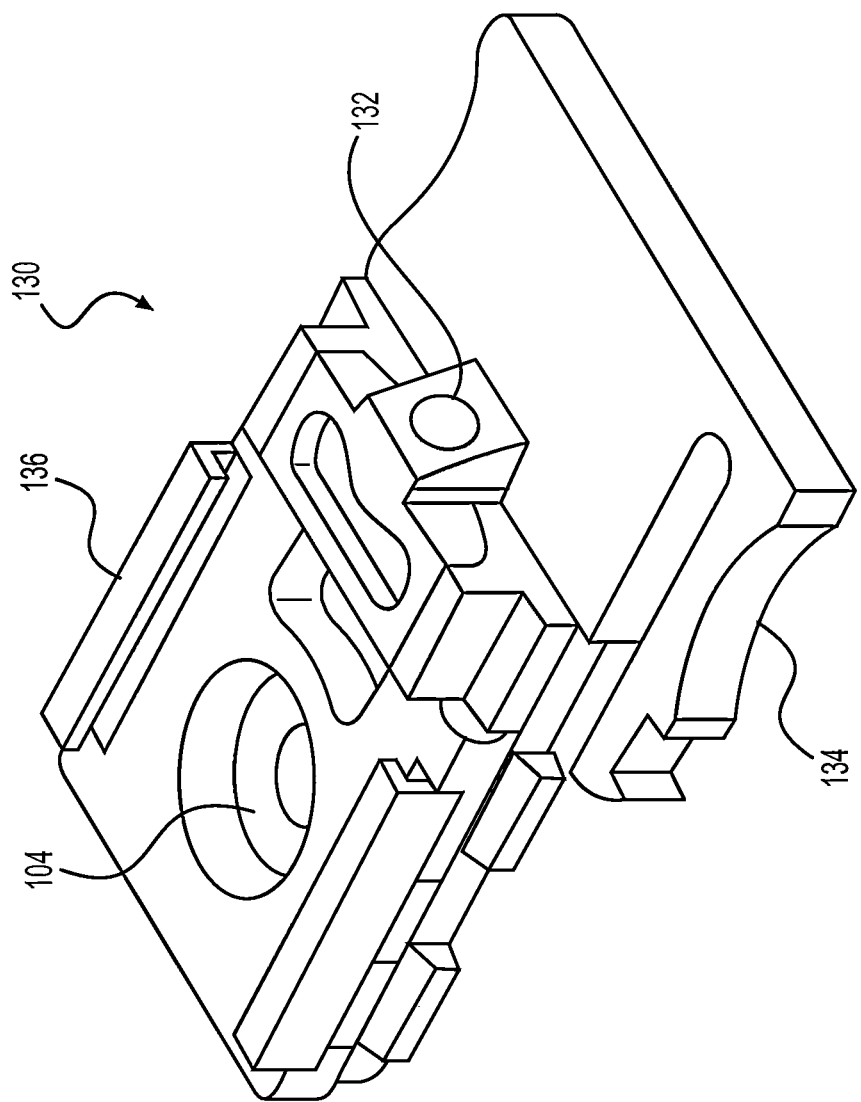

FIG. 14 is a perspective view of a cartridge 130, which shows additional features of an injection port and a retaining clip. In this case it is shown without a lid, showing a fluid injection port 132 at one end of a passageway to the well and retaining clip 134 for retaining the cartridge in the receiver. Upward and inward extending opposite guide rails 136 hold a lid 106, such as shown in FIGS. 11A-13B.

Figure 15:
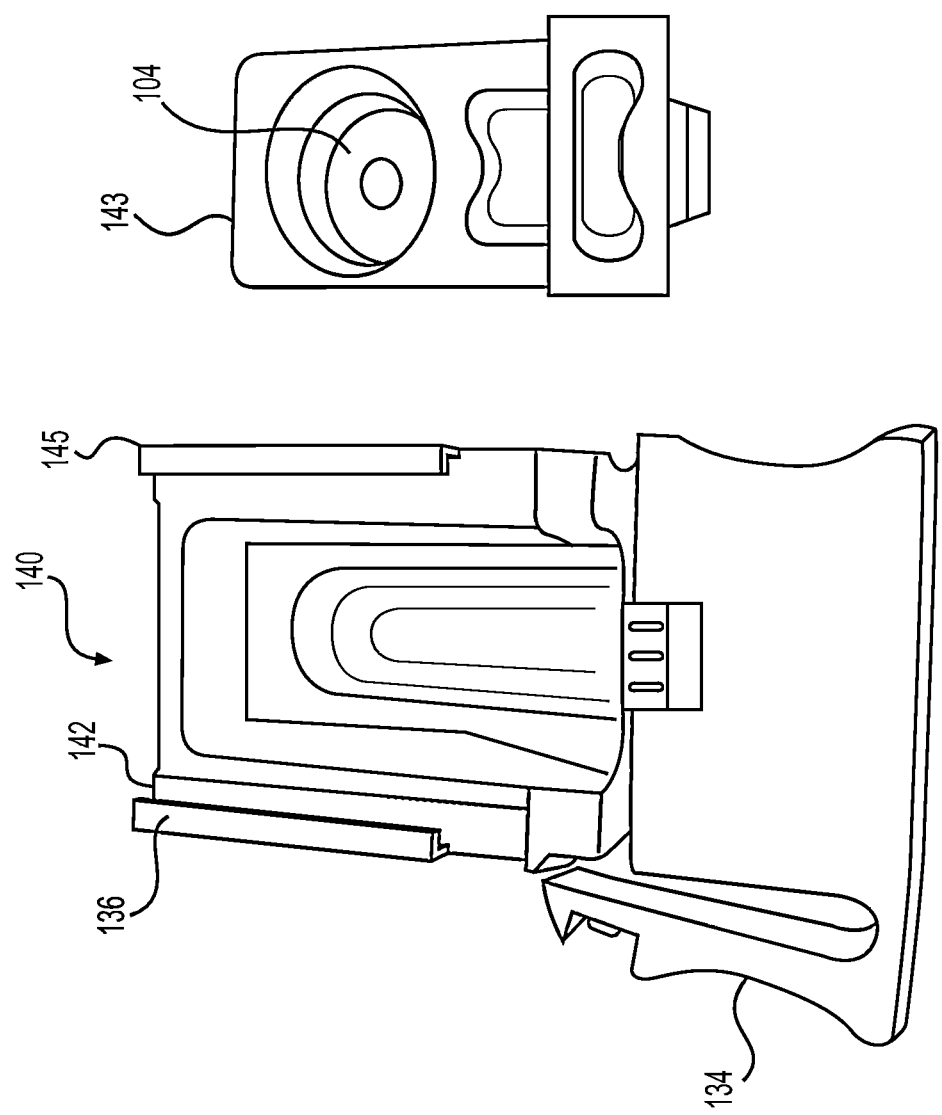

FIG. 15 shows a two-piece injection construction of a cartridge 140 platform 142 for compatibility with manufacture by injection molding. Inner part 143 holds the well 104, and outer part 145 has the retaining clip 134 and the guide rails 136.

Figure 16:
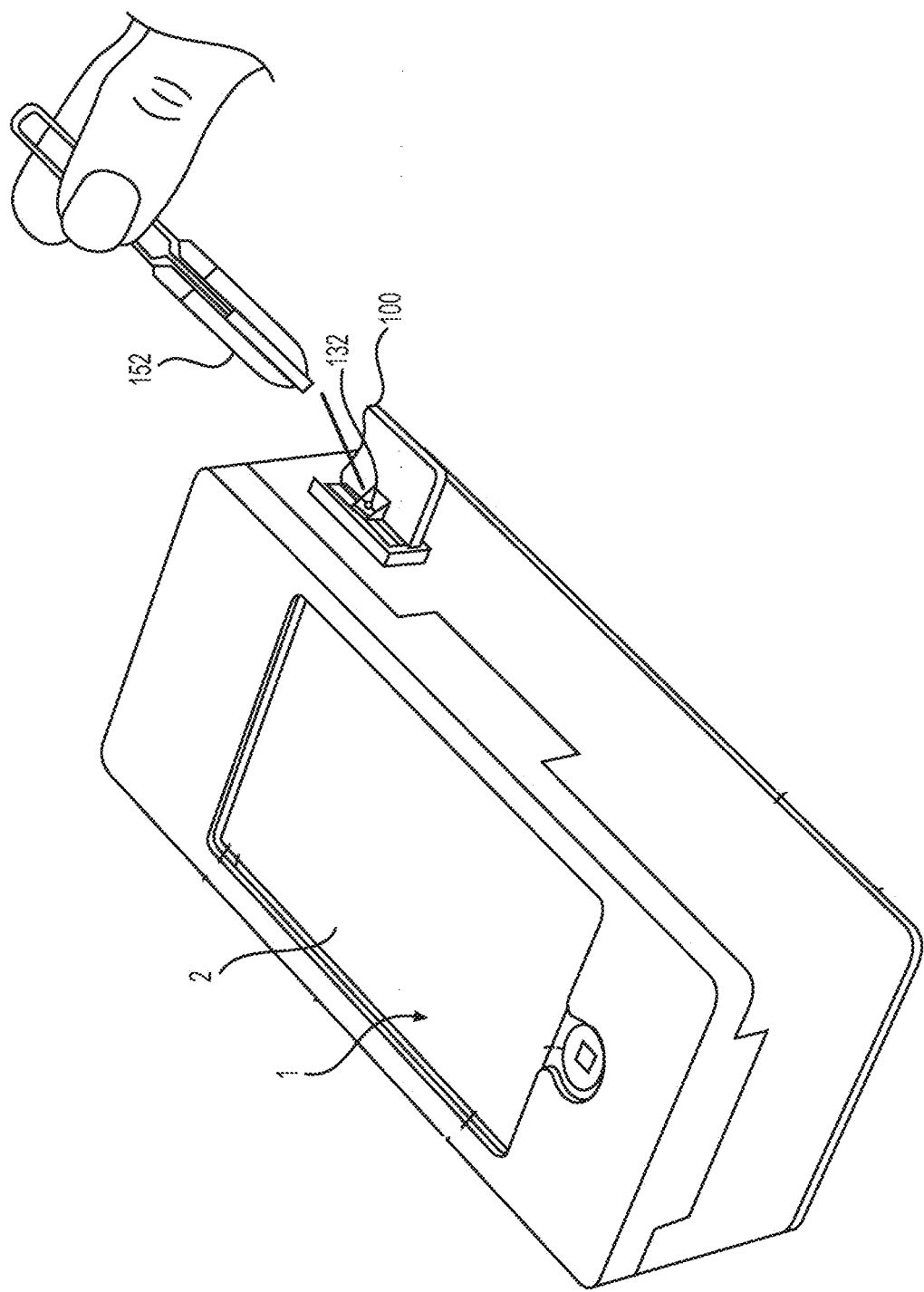
FIG. 16 shows loading protocols and the coagulation profiler with a disposable cartridge inserted and a blood sample ready to be loaded in a port in a portion of the cartridge extended from the case, according to some embodiments.

FIG. 16 shows loading protocols and the coagulation profiler with a disposable cartridge 100 inserted and a blood sample 152 ready to be loaded in a port 132 in a portion of the cartridge extended from the case. Also shown are smartphone 1 with display 2.

Figure 17:
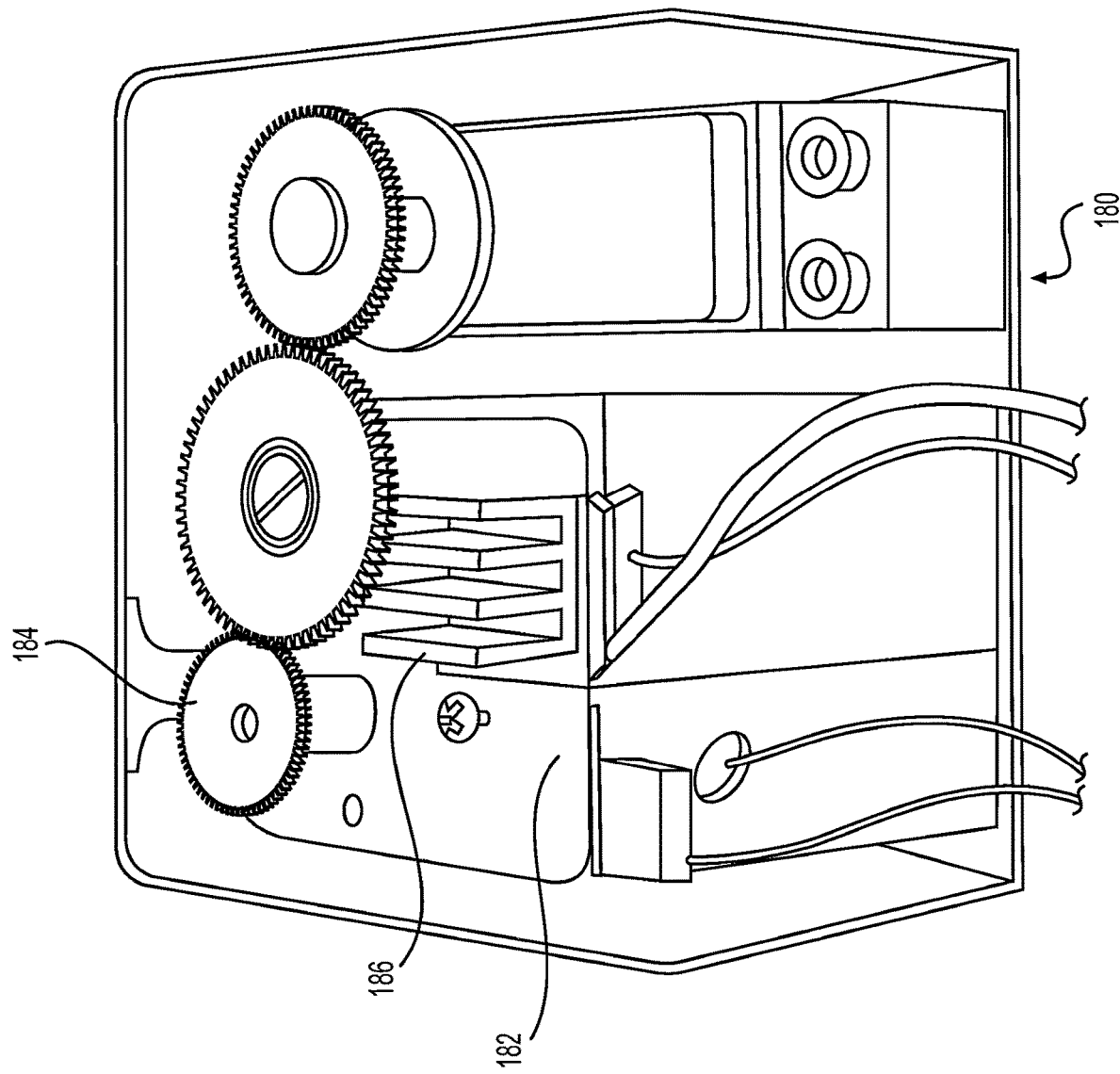
FIG. 17 shows a reciprocating motor with reduction gears and temperature controlling fins mounted on the motor housing, according to some embodiments.

FIG. 17 shows a reciprocating motor 180 with reduction gears 184 and temperature controlling fins 186 mounted on the motor housing 182.

Figure 18:
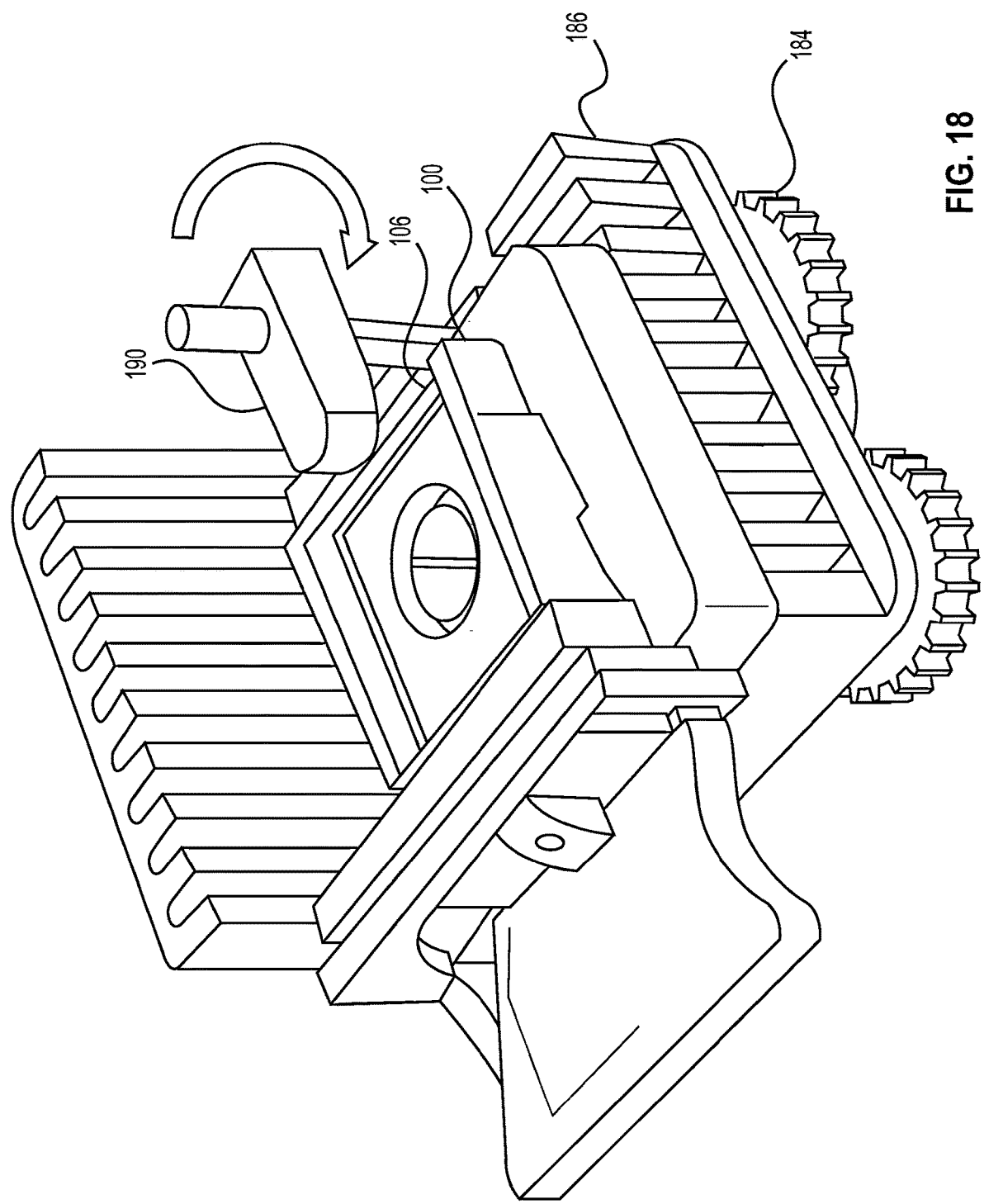
FIG. 18 shows the reduction gearing and extended fins of the temperature controller near the cartridge and a pusher connected to the reduction gears for pushing a lid back onto the cartridge for dislodging and dropping the magnetized disk on blood in the cartridge well, according to some embodiments.

FIG. 18 shows the reduction gearing 184 and extended fins 186 of the temperature controller near the cartridge 100 and a pusher 190 connected to the reduction gears for pushing a lid 106 back onto the cartridge 100 for dislodging and dropping the magnetized disk on blood in the cartridge well.

Figure 19:

FIG. 19 illustrates a non-limiting example of a smartphone interface for a medical analyzer.

Figure 20:
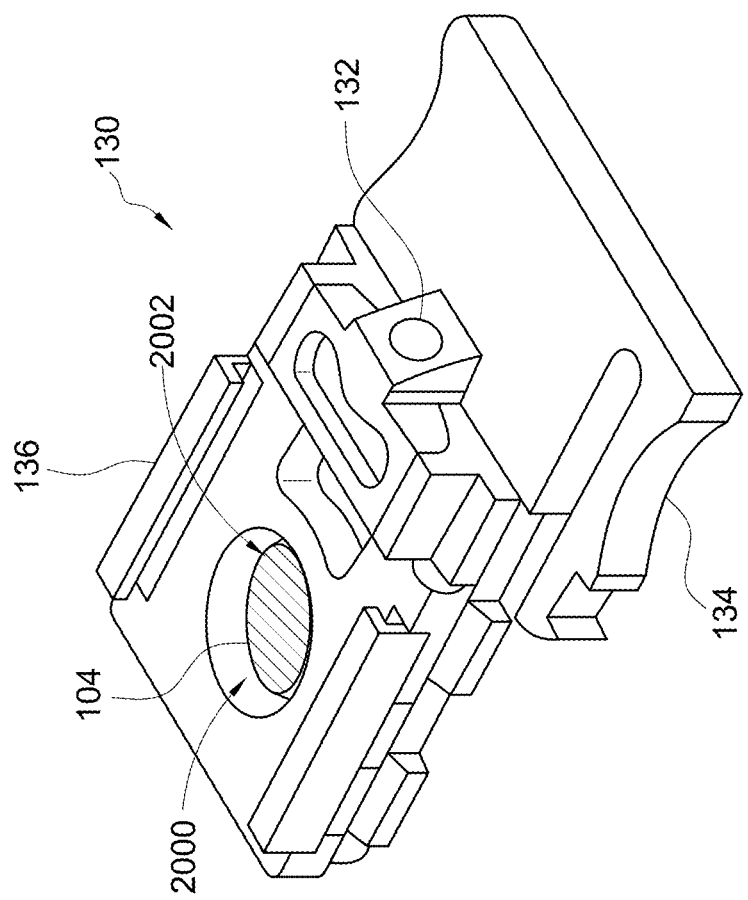

FIG. 20 schematically illustrates features of a cartridge similar to that described and illustrated in connection with FIG. 14, with a well including a well wall 2000 (sidewall) and a well floor 2002 including a perimeter defining a base of the well sidewall 2000. In some embodiments, the well floor 2002 can be relatively hydrophilic, while the well wall 2000 can be relatively hydrophobic.

Liquid can form a meniscus, defined as the curve in the upper surface of a liquid close to the surface of the container or another object, caused by surface tension. It can be either concave or convex, depending on the liquid and the surface. A concave meniscus occurs when the particles of the liquid are more strongly attracted to the container (adhesion) than to each other (cohesion), causing the liquid to climb the walls of the container. This occurs between, for example, water and glass. Water-based fluids also have a concave meniscus in glass or other wettable containers. Conversely, a convex meniscus occurs when the particles in the liquid have a stronger attraction to each other than to the material of the container. Convex menisci occur, for example, between mercury and glass in barometers and thermometers. Further details regarding equations relating to meniscus dimensions and other properties that can be controlled according to a desired clinical result are described in FIG. 21. FIG. 22 illustrates schematically a disc positionable with respect to the meniscus of a fluid sample. The well wall and/or floor can be made or coated with materials having controllable properties with respect to water (e.g., relatively hydrophilic or hydrophobic) depending on the desired clinical result. As illustrated, in some embodiments, the well floor can be relatively hydrophilic, while the well wall can be relatively hydrophobic with respect to the well floor, resulting in a disc that can be acceptably be positioned substantially parallel to the well floor (center illustration), and otherwise angled with respect to the well floor if the well wall and/or floor are too hydrophobic (right illustration) or hydrophilic (left illustration). In some embodiments, the well wall and/or the well floor are configured such that the longitudinal axis of the disc is parallel to, or angled to within about 20, 15, 10, 9, 8, 7, 6, 5, 4, 3, 2, 1, or less degrees with respect to the longitudinal axis of the well floor.

FIG. 23 schematically illustrates discs positioned within a well of a clear (relatively transparent cartridge) and illustrating proper central positioning of the disc (left and right drawings) and offset positioning of the disc (center) relating to a well wall and/or floor that is too hydrophilic and/or hydrophobic, respectively.

In some embodiments, a specific ratio of well wall and/or floor can be created to form a meniscus of particular dimensions. Also, a specific ratio of disc to well size can allow for creation of automatic positioning of the disc.

In some embodiments, the hydrophobicity or hydrophilicity of a well wall and/or floor can be controlled using a coating. In some embodiments, the hydrophobicity or hydrophilicity of a well wall and/or floor can be controlled using surface texturing features such as roughening, sintering, laser, chemical, or other etching, and the like. When the proper hydrophobic coating is applied to the well wall, the optimal meniscus is achieved at a defined volume. As the volume increases and approaches the lip of well, it becomes less concave and eventually becomes convex as it reaches the lip of the well. Therefore, in some cases the disk will only be centered in the well when the optimum volume is reached. By tracking the location of the disk as fluid is introduced, the volume of the well is indirectly measured. This relationship can be used to automate the injection of the fluid sample.

In some embodiments, the diameter of the disk is optimized for the particular meniscus and desired fluid volume. In this case the ratio of disk diameter to well diameter and well depth can be determined.

In some embodiments, the disk diameter can be, for example, between about 3 mm and about 15 mm, between about 5 mm and about 9 mm, between about 6 mm and about 8 mm, or about, at least about, or no more than about 2, 3, 4, 5, 6, 7, 8, 9, 10, 11, 12, 13, 14, 15, 16, 17, 18, 19, 20 mm, or more or less, or ranges including any two of the foregoing values.

In some embodiments, the well diameter (e.g., at the top or bottom of the well) can be, for example, between about 4 mm and about 25 mm, between about 6 mm and about 15 mm, between about 8 mm and about 12 mm, or about, at least about, or no more than about 3, 4, 5, 6, 7, 8, 9, 10, 11, 12, 13, 14, 15, 16, 17, 18, 19, 20, 21, 22, 23, 24, 25 mm, or more or less, or ranges including any two of the foregoing values.

In some embodiments, the well depth can be, for example, between about 0.5 mm and about 8 mm, between about 1 mm and about 6 mm, between about 1.5 mm and about 3 mm, or about, at least about, or no more than about 0.5, 1, 1.5, 2, 2.5, 3, 3.5, 4, 4.5, 5, 5.5, 6, 6.5, 7, 7.5, 8 mm, or more or less, or ranges including any two of the foregoing values.

In some embodiments, the disk diameter to well diameter ratio can be, for example, between about 0.5 and about 1.0, between about 0.6 and about 0.8, or about 0.3, 0.4, 0.5, 0.6, 0.7, 0.8, 0.9, 1.0, or ranges including any two of the foregoing values.

In some embodiments, the well diameter to well depth ratio can be, for example, between about 3.0 and about 6.0, between about 4.0 and about 5.0, or about 2.5, 3.0, 3.5, 4.0, 4.5, 5.0, 5.5, 6.0, 6.5, 7.0, 7.5, 8.0, or ranges including any two of the foregoing values.

In some embodiments, the hydrophobicity is optimized for blood, however other fluids (e.g., urine, saliva, or other body fluids) may require variations in the hydrophobicity to achieve the desired meniscus.

One embodiment of the induced disc rotation would progressively reduce the range of motion to improve sensitivity. For instance, at the beginning of the test the motion induced would be +/−20 degrees. Since the range of motion is larger, smaller amounts of change are more easily detected and since the fibrin and platelets have yet to form a clot, the excess motion will not destroy the clot.

In an alternate embodiment an absorbent coating or material can be used to wick the fluid across the well floor. This provides even fluid distribution while maintaining hydrophobic walls.

In an alternate embodiment multiple perforation across the well floor provide multiple points of fluid entry. This could be a few points or a large number where the well floor is essentially a mesh. This provides even fluid distribution while maintaining hydrophobic walls.

Figure 24:
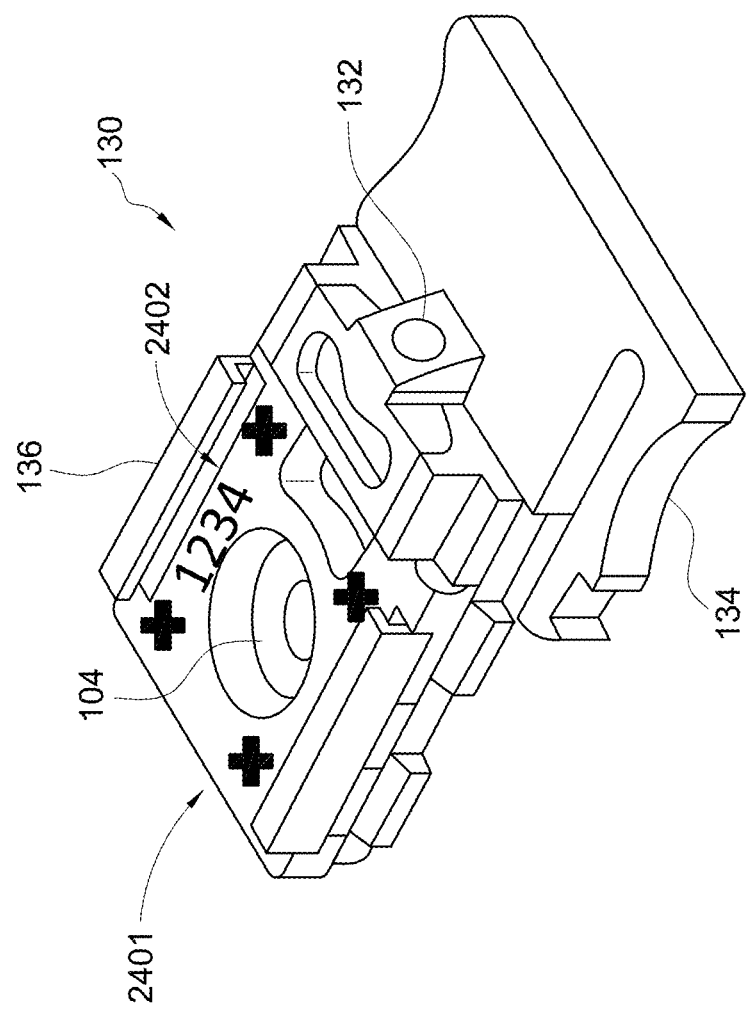

FIG. 24 schematically illustrates an embodiment of a removable and/or insertable cartridge that can include indicia 2401, such as cross-hairs to ensure that the cartridge is fully inserted into the system. A QR code, bar code, serial number, RFID chip, or similar 2402 could be printed or otherwise attached to prevent reuse and counterfeiting. In some embodiments, a holographic image could be utilized to detect distance via color or other parameters. In some embodiments, exposure to UV light could remove the QR code or similar indicia, rendering the cartridge unstable and/or marking the cartridge as being used, thus preventing reuse.

In some embodiments, the cartridge or a portion thereof could be clear, optically transparent, or optically translucent to allow light to illuminate the well and allow the viewing of the flow of the blood or other sample into the cartridge. The cartridge could include a portion that is optically opaque (e.g., a blacked-out handle) for grip, blocking light from flowing through the clear material (e.g., plastic) and sealing the gap between the cartridge and the slot.

In some embodiments, such as shown in FIG. 25, calibrations can be performed to better ensure more accurate distance placement (proximity) between the cartridge containing the disk and the magnet which induces motion. Since the location of the magnetometer is fixed in the system, the relative magnetic field measured is representative of the components, e.g., three components being in the proper alignment. Likewise the actuation can be measured since it will change the magnetic field over time. Therefore if a sinusoidal waveform is of sufficient amplitude and frequency, the magnet can be the proper strength, in the proper location and oscillating over the proper range. The disc can be positioned within the cartridge when inserted into the analyzer system. A sensor such as a magnetometer within the imaging device (e.g., smartphone camera for example) or elsewhere could be utilized and calibrations can be performed. Example traces X, Y, and Z are shown, with trace Z illustrating a higher amplitude and potentially proper proximity, while traces X and Y are lower amplitude which may indicate a troubleshooting issue, e.g., improper proximity. Calibration and/or the magnetic field can lead to better clinical results, and an acceptable trace as illustrated and described previously in connection with FIG. 2A above.

In some embodiments, it can be advantageous to include a tracking point impervious to motion, as illustrated and described in connection with FIG. 1F. Localized tracking and reference point(s) can be co-located making it impervious to induced motion.

In some embodiments, the disc material density is between about 1.0 and about 1.5 $g/cm^3$, such as between about 1.10 and about 1.30 $g/cm^3$, between about 1.20-1.22 $g/cm^3$, about 1.15, 1.16, 1.17, 1.18, 1.19, 1.20, 1.21, 1.22, 1.23, 1.24, 1.25 $g/cm^3$, or ranges incorporating any two of the aforementioned values. In some embodiments, the permeability of the disk is zero or substantially zero. In some embodiments, an insert should extend partially or completely along the diameter or substantially the diameter of the disk with a ratio of about 15/1, 20/1, 25/1, 30/1, or ranges incorporating any of the foregoing values, and relative to the diameter of the disc. In some embodiments, the insert can have a permeability of between about $1\times10^{-4}$ d or $m^2$ and about $6.3\times10^{-3}$ d or $m^2$, between about $1\times10^{-4}$ d or $m^2$ and about $6.3\times10^{-3}$ d or $m^2$ or less than about $6.3\times10^{-3}$ $m^2$ in some embodiments.

FIG. 26 illustrates an embodiment of a sample analysis system including an insertable cartridge that can be utilized for blood typing. In some embodiments, a plurality, such as 3, 4, or more separate compartments can be placed in a single well, each compartment having one, two or more reagents therein (e.g., 4 cartridges with 4 reagents; 1 reagent per cartridge). Each compartment or sub-well can include its own branch of an injection port, and have a defined shape, such as a triangular shape as shown, or other shapes (e.g., square, rectangular, rhomboid, trapezoidal, oval, circular, and others). A convex meniscus can provide a spherical shape to pull agglutination into the center of the mass. The triangular shape of hydrophobic well sections can remain a triangle of a blood-water (or other fluid/reagent) mixture. When agglutination occurs (positive typing), a circular shape can form as noted above. If no agglutination is present (negative typing), the well section including the sample can remain a triangular shape.

FIG. 27 schematically illustrates an embodiment of an insertable cartridge that can include a luer lock (at arrow apex) or other port (left figure) for connecting a syringe containing a sample. In some embodiments, the cartridge could be connectable to a tube (right figure) with a luer lock or other port spaced apart from the cartridge as shown.

Figure 28:
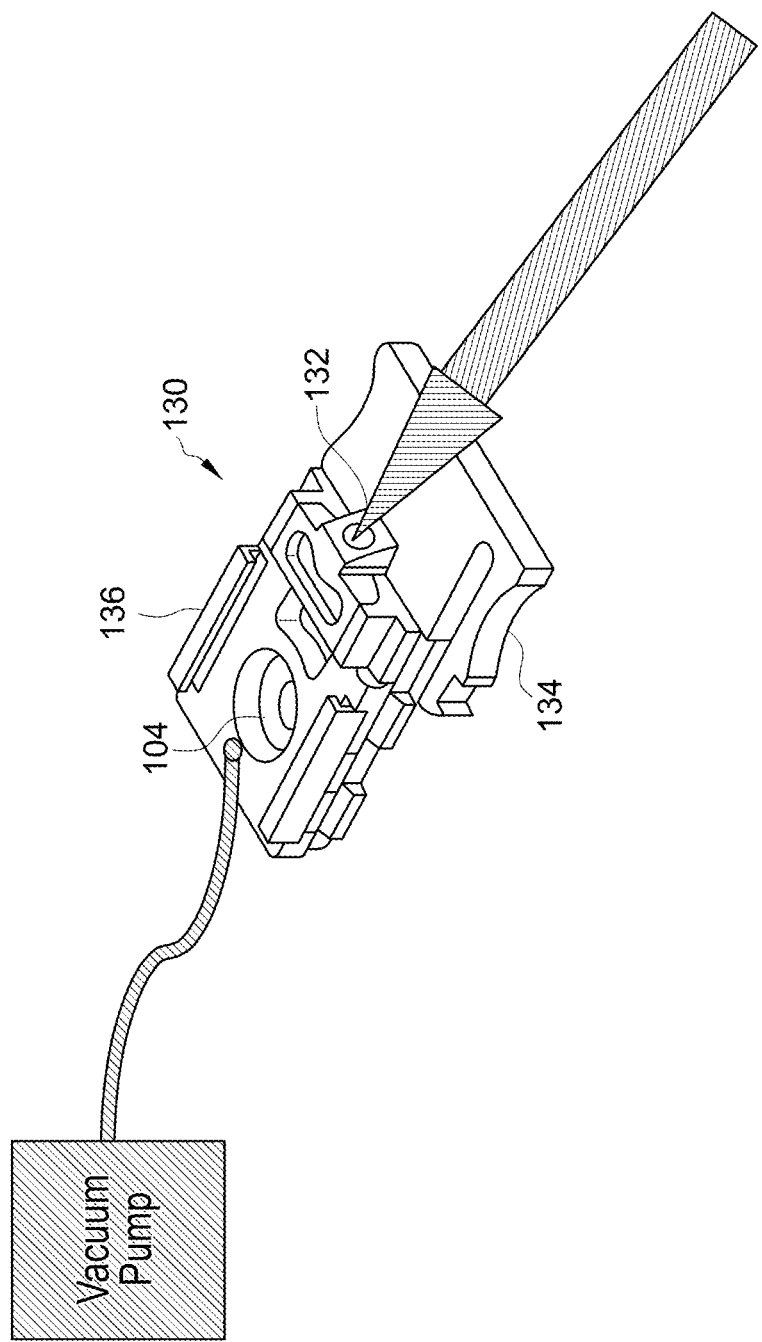

FIG. 28 schematically illustrates an embodiment in which an insertable cartridge can include a sealed cartridge vacuum port. A vacuum pump can be in fluid communication with the sample well to allow a sample to flow into the well from the input port of the cartridge.

In some embodiments, the cartridge could be configured for a wide variety of applications, including but not limited to a catalase reaction, coagulase reaction, quick crossmatch, LAL detection, PT/INR, ACT, PTT, and the like. In some embodiments, a cartridge could include concentric wells configured for platelet mapping.

In some embodiments, disclosed herein are systems and methods that can include magnetic couplings to maximize induced torque on a measuring disk.

In some embodiments, as illustrated schematically in FIG. 29A, a small magnet, which can include a rectangular, cylindrical, or other geometry magnet 2901, such as a bar magnet for example, can be aligned in parallel with another magnetically compatible structure, such as, for example, a ferrous metal of similar dimensions 2902. In some embodiments, the magnetically compatible structure can be a steel wire 2902. The magnet 2901 and steel wire 2902 can be in close proximity such that they magnetically couple together. In some embodiments, the wire 2902 is embedded into a disk 2903 made of plastic or other material, which is held at the surface of a fluid, under test. FIG. 29A illustrates wire 2902 separated from the disk 2903. FIG. 29B illustrates wire 2902 embedded in the disk 2903.

The use of a bar magnet 2901 can advantageously allow for greater torque to be applied to an object to be controlled by magnetic coupling, such as, for example, disk 2903.

The use of a bar magnet 2901 can also allow for a progressive decoupling profile that is similar in practice to that of a torsion wire.

Magnetically induced torque can be applied and this torque can decrease progressively as the wire and the bar magnet are made more perpendicular to one another as the viscoelasticity in the test material increases.

This technique allows the system to apply a desired torque that does not exceed the strength of the clot while it is forming, while decreasing observable/measurable motion of the disk.

The fluid starts off as a low friction interface and the disk rotates with any motion of the disk.

In some embodiments the magnet 2901 is a neodymium (N42) cylindrical magnet that is about 0.125" diameter× about 0.2" thick.

In some embodiments, the magnet can have a diameter of between about 0.01" and about 1", about 0.01", 0.02", 0.03", 0.04", 0.05", 0.06", 0.07", 0.08", 0.09", 0.10", 0.11", 0.12", 0.13", 0.14", 0.15", 0.16", 0.17", 0.18", 0.19", 0.20", 0.21", 0.22", 0.23", 0.24", 0.25", 0.30", 0.35", 0.40", 0.45", 0.50", or more or less, or ranges including two of the foregoing values.

In some embodiments, the magnet can have a thickness of about 0.01", 0.02", 0.03", 0.04", 0.05", 0.06", 0.07", 0.08", 0.09", 0.10", 0.11", 0.12", 0.13", 0.14", 0.15", 0.16", 0.17", 0.18", 0.19", 0.20", 0.21", 0.22", 0.23", 0.24", 0.25", 0.30", 0.35", 0.40", 0.45", 0.50", or more or less, or ranges including two of the foregoing values.

In some embodiments, the surface field strength of the magnet is about 6300 Gauss. In some embodiments, the surface field strength of the magnet is between about 4,000 Gauss and about 10,000 Gauss, such as about 4,000, 4,500, 5,000, 5,500, 6,000, 6,500, 7,000, 7,500, 8,000, 8,500, 9,000, 9,500, or 10,000 Gauss or more or less, or ranges including any two of the foregoing values.

In some embodiments, the wire 2902 is about 0.04" in diameter and about 0.25" inches in length. In some embodiments, the wire 2902 is about 0.01", 0.02", 0.03", 0.04", 0.05", 0.06", 0.07", 0.08", 0.09", 0.10", or more or less in diameter, or ranges including any two of the foregoing values. In some embodiments, the wire 2902 is about 0.05", 0.10", 0.15", 0.20", 0.25", 0.30", 0.35", 0.40", 0.45", 0.50" or more or less, or ranges including any two of the foregoing values.

Figure 29C:
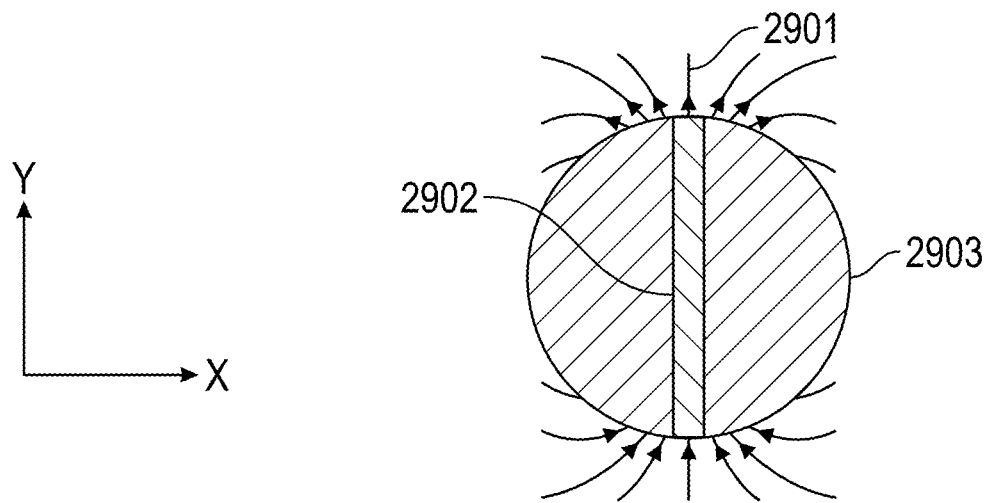
Figure 29D:
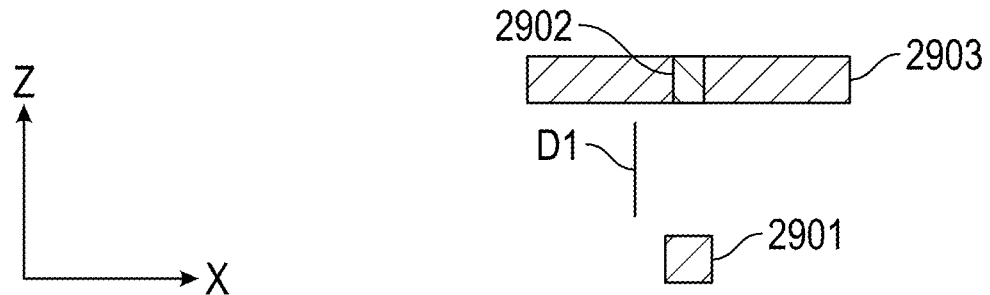

FIGS. 29C-29D schematically illustrate views of embodiments of the magnet 2901, wire 2902, and disk 2903 with the Y-X and Z-X planes shown for reference.

The distance D1 between the magnet 2901 and wire 2902 can be fixed in some embodiments, and be about 0.25" in some cases, or about 0.05", 0.10", 0.15", 0.20", 0.25", 0.30", 0.35", 0.40", 0.45", 0.50" or more or less, or ranges including any two of the foregoing values.

In some embodiments, the distance D1 between the magnet and wire can be calibrated to have optimum coupling and minimal pull force down on the disk.

In some embodiments, the distance D1 can be configured such that the pulldown force is less than the surface tension and/or buoyancy of the disk 3.

In other embodiments, the dimensions of the elements can be changed to include similar coupling relationships where torque is maximized and the pulldown force is minimized to balance the surface tension.

In some embodiments, systems and methods are disclosed for measuring viscoelasticity of two blood (fluid) samples. In some embodiments as schematically illustrated in FIGS. 30A-30D, a device can include any number of wire, e.g., steel wire 3001, center (inner) disk 3002, center (inner) well 3003, outer disk 3004 and outer well 3005. The apparatus can be configured in a concentric manner with a wire 3001 embedded into the middle of center disk 3002. The center disk 3002, is nested in the center well 3003, and the center well 3003 is within the outer disk 3004. The outer disk 3004 is nested within the outer well 3005. The center well 3003 can be filled with a first biological sample, e.g., blood sample and a reagent. The outer well 3005 can be filled with a second biological sample, e.g., blood sample and a reagent, which can be the same as, or different from the first blood sample and the first reagent. This allows two biological, e.g., blood samples to be tested simultaneously or a single blood sample to be tested using different reagents.

The center disk 3002 can be surrounded by the fluid in the center well 3003, and the outer disk 3004 is surrounded by a fluid in outer well 3005.

Figure 30A:
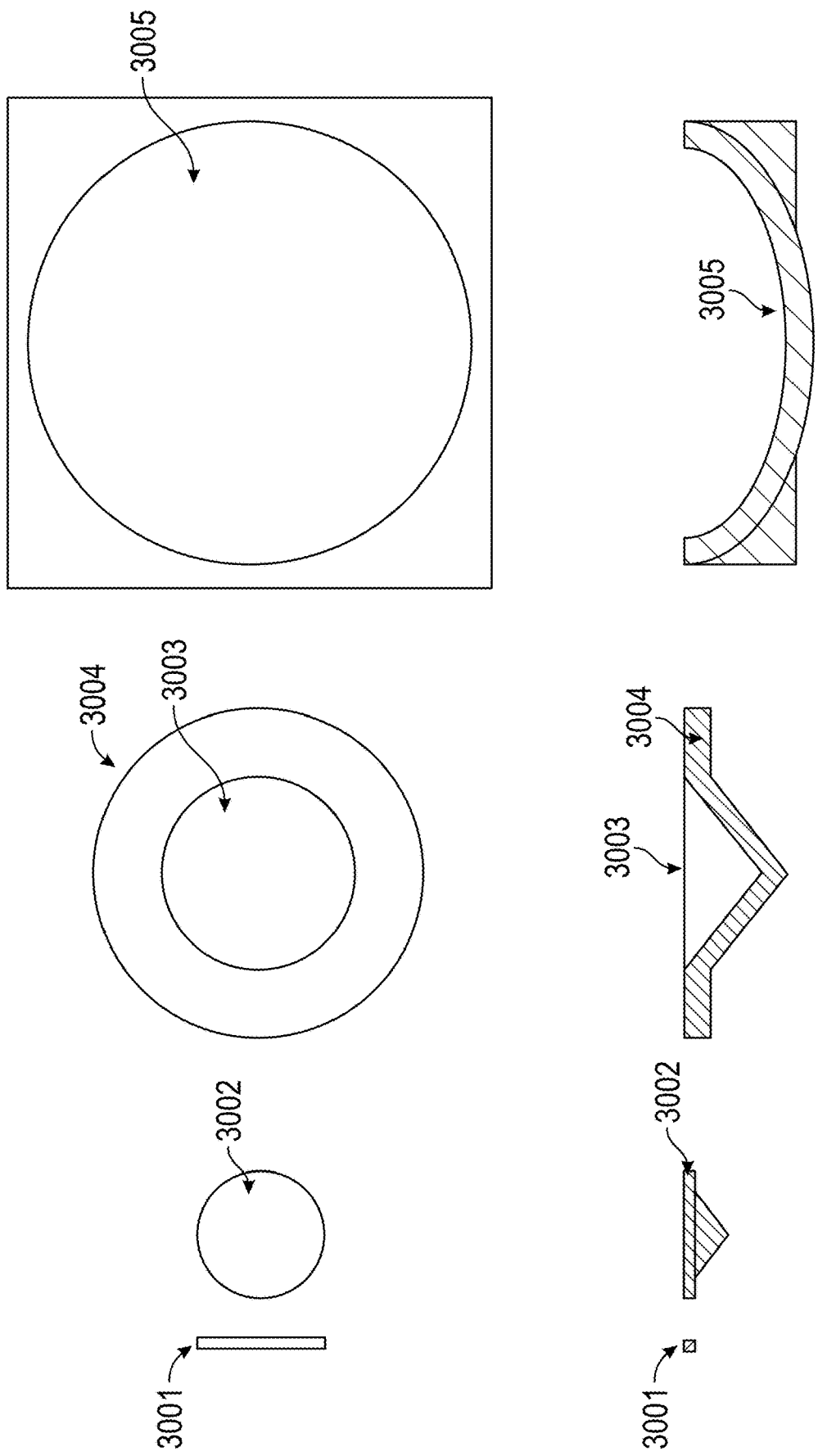
Figure 30B:
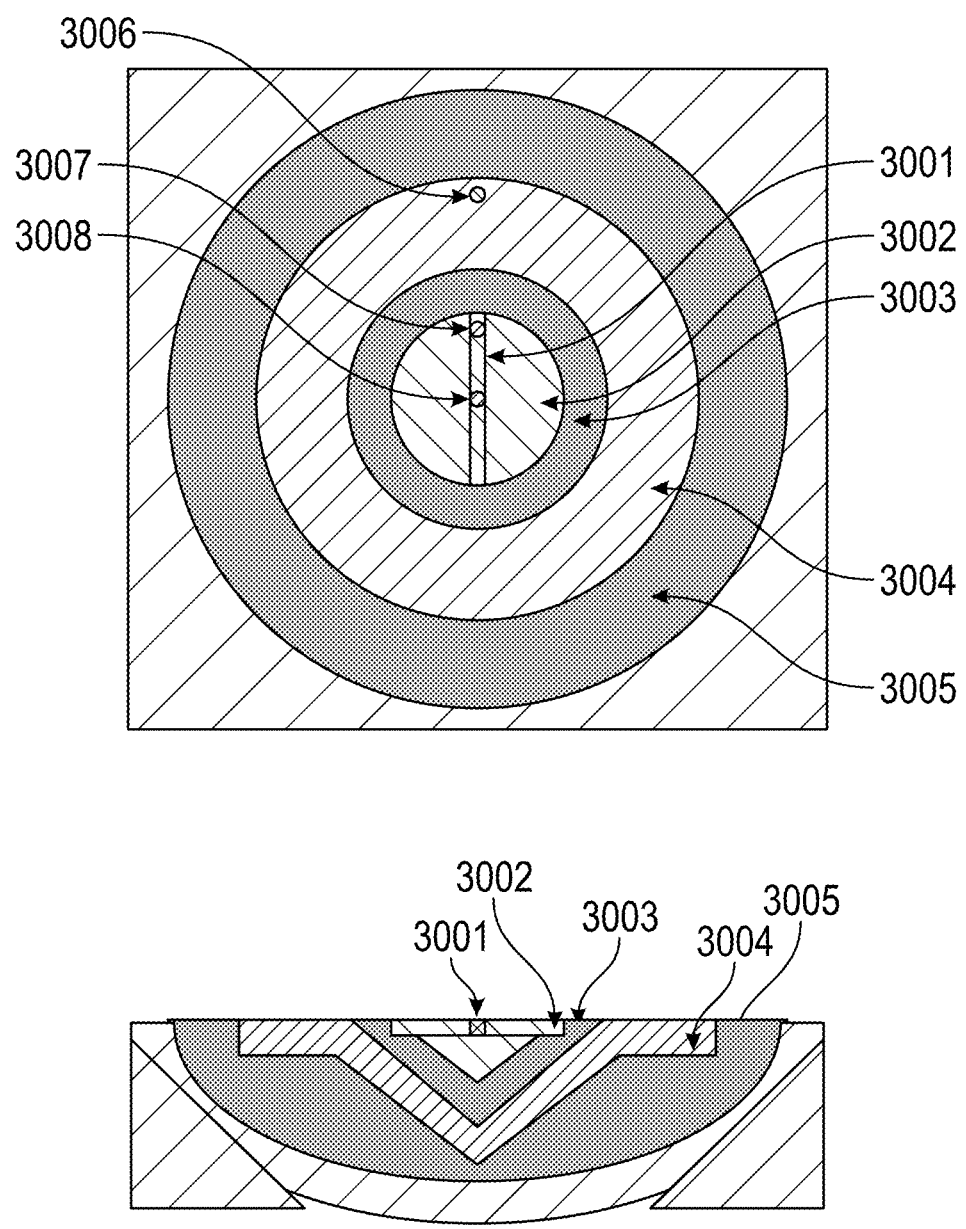

As shown schematically in FIG. 30B, in some embodiments, the center disk is magnetically actuated to rotate over a desired angular distance. This rotation can be repeated over a set time period, in one embodiment about every ten seconds, or about, at least about, or no more than about 5, 10, 15, 20, 25, 30, 35, 40, 45, 50, 55, 60 seconds, or more or less, or ranges including any two of the foregoing values. The motion induced can be dependent on the state of the viscoelasticity of the blood sample. As the blood sample in the center well 3003 coagulates, the motion of the center disk 3002, relative to the outer disk 3004 decreases. As the blood sample in the center well 3003 coagulates, the center disk 3002 couples motion to the outer disk 3004. The degree of motion coupled is proportional to the amount of coagulation. The outer disk 3004 can now rotate in the fluid sample contained in the outer well 3005. The net motion coupled to the outer disk 3004 is a function of both blood samples. Three tracking points are used to record relative motion, 3006, 3007, and 3008. The outer tracking point 3006 can be located on the perimeter of the outer disk 3004. The inner tracking point 3007 can be located on the perimeter of the center disk 3002. The pivot point 3008 is located at the middle of the center disk 3002.

In one embodiment, the center well 3003 can be filled with a blood sample and a reagent such as, for example, tissue factor. The outer well 3005 includes the same blood sample however the reagents used are platelet inhibitors such, for example, Abciximab and cytochalasin D. These platelet inhibitors only allow fibrin to contribute to the clot and therefore the clot strength is significantly less than the clot forming in the center well 3003. This assay can be clinically relevant in comparing the two clot strengths. Identifying an irregular clot strength in the center well 3003, can be obtained using the pivot point 3008 and the inner tracking point 3007. Furthermore, the motion observed using the outer tracking point 3006 and the pivot point 3008 can provide the fibrin clot strength. An abnormally weak clot strength in the other well can be indicative of a lack of fibrin.

In some embodiments, a system can include additional, such as 3, 4, 5, 6, 7, 8, or even more concentric disks and wells, each additional disk including one or more discrete tracking points. Such embodiments can be advantageous in efficiently assessing at least 3, 4, 5, 6, 7, 8, or more biological samples at once in the same system.

In some embodiments, assessment of biological sample parameters, such as coagulation for example, can be achieved by assessing linear, rather than rotational motion.

Figure 30C:
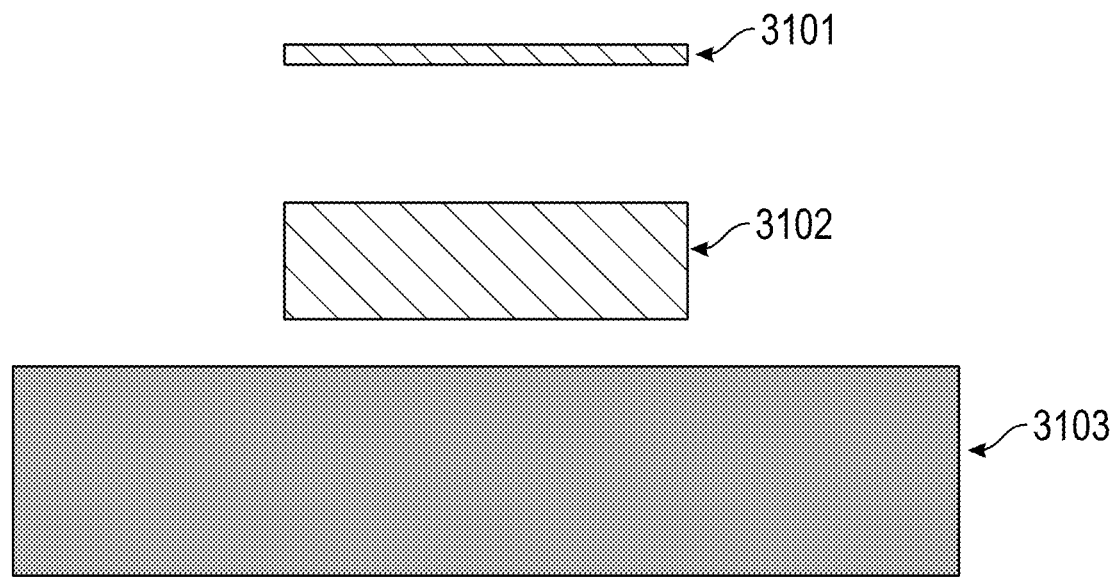
Figure 30D:
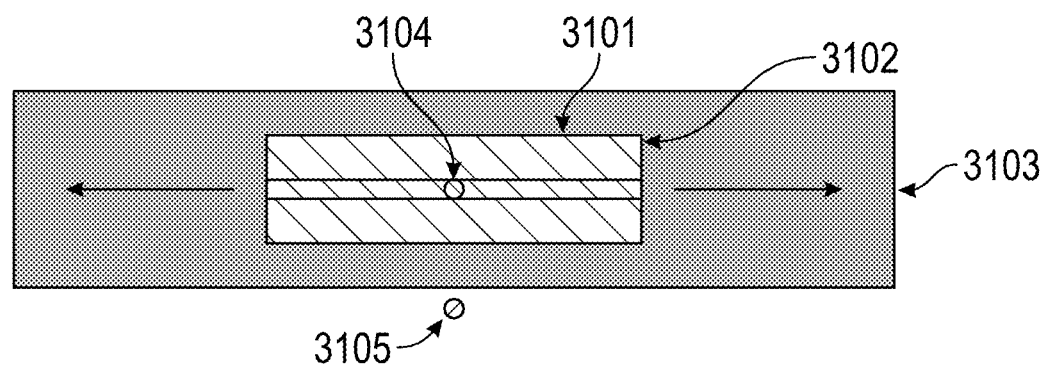

With reference to FIGS. 30C and 30D, in some embodiments a well 3103 that can be rectangular shaped in some cases can be used in conjunction with an element 3102 with the same or similar geometry (e.g., rectangular) that is embedded with a wire, such as a steel wire 3101. In this embodiment the rectangular element 3012 is actuated magnetically back and forth in a blood sample and in certain embodiments along a linear path. As the blood sample coagulates the motion is reduced and viscoelasticity can be measured using the tracking point 3104 and the relative point 3105. The motion can also be observed absolutely using only point 3104.

The foregoing description and examples has been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning a disc within a sample well" include "instructing positioning of a disc within a sample well."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A method for measuring coagulation of a liquid, comprising:
   activating a portable measuring device;
   injecting a liquid sample into a well within a cartridge, the well comprising a sidewall and a floor;
   inserting the cartridge with the liquid sample into the portable measuring device;
   providing a contactless magnetic coupling, wherein a disc is positioned within the well of the cartridge within the portable measuring device;
   reciprocating the well or the disc within the well with the contactless magnetic coupling over an angular sweep range;
   illuminating the disc;
   observing the disc with a video camera;
   recording times of changes in movement of the disc; and
   reducing the angular sweep range of the contactless magnetic coupling to follow a reduction in motion caused by coagulation of the liquid sample, wherein reducing the angular sweep range is based at least in part on the recorded changes in movement of the disc, wherein the angular sweep range changes to optimize sensitivity of different phases of coagulation and maintain a constant induced torque profile.

2. The method of claim 1, wherein the reciprocating comprises reciprocating the disc with the contactless magnetic coupling, and the recording comprises recording time differentiation between a start of movement of the disc and slowing and stopping of movement of the disc.

3. The method of claim 1, further comprising placing the disc in the well after the injecting of the liquid sample.

4. The method of claim 1, wherein the turning on activating comprises connecting a power source to a motor for the reciprocating, and starting the illuminating and the video camera and a central processor for recording times of changes in movement of the disc and creating displays according to the changes in movement of the disc.

5. The method of claim 4, wherein starting the illuminating, the video camera and the central processor comprises turning on a smartphone connected to the portable measuring device.

6. The method of claim 1, wherein reducing the angular sweep range comprises reducing the angular sweep range proportional to a recorded rotational sweep movement of the disc at a point in time following initiation of reciprocating the well or the disc.

7. The method of claim 6, wherein adjusting reducing the angular sweep range comprises adjusting reducing the angular sweep range substantially equal to a recorded rotational sweep movement of the movable device disc.

8. The method of claim 1, wherein illuminating the disc comprises illuminating with LED light.

9. The method of claim 1, wherein illuminating the disc comprises illuminating with UV light.

10. The method of claim 1, wherein the disc comprises ferrous metal.

11. The method of claim 1, wherein the disc comprises a wire.

12. The method of claim 11, wherein the wire comprises steel.

13. The method of claim 1, further comprising controlling internal temperature in the measuring device.

14. The method of claim 13, wherein controlling the internal temperature in the portable measuring device comprises synchronizing the internal temperature with a body temperature of a patient from which the liquid sample was obtained from.

15. A system for measuring coagulation of a liquid, comprising:
    a portable measuring device;
    a controller;
    a light source operably associated with the measuring device;
    a video camera;
    a cartridge comprising a well and a disc, the cartridge configured to be inserted into a receptacle of the portable measuring device, the well configured to house a liquid sample therein, and the disc positioned within the well;
    a magnetic actuator configured to reciprocate the well or the disc within the well via a contactless magnetic coupling over an angular sweep range;
    wherein the video camera is configured to record times of changes in movement of the disc; and
    wherein the controller is configured to regulate the magnetic actuator by reducing the angular sweep range of the contactless magnetic coupling to follow a reduction in motion caused by coagulation of the liquid sample, wherein reducing the angular sweep range is based at least in part on recorded changes in movement of the disc, wherein the angular sweep range changes to optimize sensitivity of different phases of coagulation and maintain a constant induced torque profile.

16. The system of claim 15, wherein reducing the angular sweep range comprises reducing the angular sweep range proportional to a recorded rotational sweep movement of the disc at a point in time following initiation of reciprocating the well or the disc.

17. The system of claim 15, wherein reducing the angular sweep range comprises reducing the angular sweep range substantially equal to a recorded rotational sweep movement of the disc.

18. The system of claim 15, wherein the controller is configured to synchronize an internal temperature in the portable measuring device with a body temperature of a patient from which the liquid sample was obtained from.

19. The system of claim 15, wherein the controller is configured to regulate an internal temperature in the measuring device.

* * * * *

UNITED STATES PATENT AND TRADEMARK OFFICE
CERTIFICATE OF CORRECTION

PATENT NO. : 12,277,814 B2
APPLICATION NO. : 17/759161
DATED : April 15, 2025
INVENTOR(S) : Luke B. Joseph Page 1 of 1

It is certified that error appears in the above-identified patent and that said Letters Patent is hereby corrected as shown below:

In the Claims

Column 25, Line 62, Claim 4, delete "wherein the turning on activating" and insert -- wherein the activating --.

Column 26, Line 10, Claim 7, delete "wherein adjusting reducing the" and insert -- wherein reducing the --.

Column 26, Line 11, Claim 7, delete "comprises adjusting reducing the" and insert -- comprises reducing the --.

Column 26, Line 13, Claim 7, delete "of the movable device disc." and insert -- of the disc. --.

Signed and Sealed this
Fifteenth Day of July, 2025

Coke Morgan Stewart
*Acting Director of the United States Patent and Trademark Office*